(12) United States Patent
Nakayama et al.

(10) Patent No.: US 9,233,922 B2
(45) Date of Patent: Jan. 12, 2016

(54) PROCESS FOR PRODUCING N-(HETERO)ARYLAZOLES

(75) Inventors: Yuji Nakayama, Hiratsuka (JP); Tohru Kobayashi, Hiratsuka (JP)

(73) Assignee: TAKASAGO INTERNATIONAL CORPORATION, Tokyo (JP)

(*) Notice: Subject to any disclaimer, the term of this patent is extended or adjusted under 35 U.S.C. 154(b) by 3 days.

(21) Appl. No.: 14/342,570

(22) PCT Filed: Aug. 31, 2012

(86) PCT No.: PCT/JP2012/072828
§ 371 (c)(1),
(2), (4) Date: Mar. 4, 2014

(87) PCT Pub. No.: WO2013/032035
PCT Pub. Date: Mar. 7, 2013

(65) Prior Publication Data
US 2014/0371461 A1 Dec. 18, 2014

Related U.S. Application Data

(60) Provisional application No. 61/531,737, filed on Sep. 7, 2011.

(30) Foreign Application Priority Data

Sep. 2, 2011 (JP) .................................. 2011-191166
Aug. 24, 2012 (JP) .................................. 2012-185502

(51) Int. Cl.
| | |
|---|---|
| C07D 215/38 | (2006.01) |
| C07D 209/82 | (2006.01) |
| C07D 209/86 | (2006.01) |
| C07D 209/84 | (2006.01) |
| C07D 209/60 | (2006.01) |
| C07D 401/14 | (2006.01) |
| C07D 401/04 | (2006.01) |
| C07C 409/04 | (2006.01) |
| C07D 209/08 | (2006.01) |

(52) U.S. Cl.
CPC ............ *C07D 209/60* (2013.01); *C07C 409/04* (2013.01); *C07D 209/08* (2013.01); *C07D 209/86* (2013.01); *C07D 401/04* (2013.01); *C07D 401/14* (2013.01)

(58) Field of Classification Search
None
See application file for complete search history.

(56) References Cited

U.S. PATENT DOCUMENTS 5,576,460 A * 11/1996 Buchwald et al. ............ 564/386

OTHER PUBLICATIONS

Johnstone, RA. et al. Heterogeneous Catalytic Transfer Hydrogenation and Its Relation to Other Methods for Reduction of Organic Compounds. Chem. Rev. 1985, vol. 85, p. 141.*
Dorwold, FZ. Side Reactions in Organic Synthesis. Wiley. 2005, preface.*
Sames, D. et al. Direct Palladium-Catalyzed C-2 and C-3 Arylation of Indoles: A Mechanistic Rationale for Regioselectivity. JACS. 2005, vol. 127, p. 8050.*
Souharce, B. et al. Amorphous Carbazole-based (Co)polymers for OFET Application. Macromolecular Rapid Communications. 2009, vol. 30, p. 1259.*
Suzuki, K. et al. A New Hybrid Phosphine Ligand for Palladium-Catalyzed Amination of Aryl Halides. 2008, vol. 350, p. 654.*
Chen, C. et al. Arylation of Diarylamines Catalyzed by Ni(II)-PPh3 System. 2005, vol. 7, p. 2209.*
International Search Report (PCT/ISA/210) issued Dec. 5, 2012, or corresponding Application No. PCT/JP/2012/072828.
Written Opinion (PCT/ISA/237) issued Dec. 5, 2012, or corresponding Application No. PCT/JP/2012/072828.
Lane, et al; "Direct Palladium-Catalyzed C-2 and C-3 Arylation and Indoles: A Mechanistic Rationale for Regioselectivity" Journal of American Chemical Society; vol. 127, Jan. 1, 2005; pp. 8050-8057.
Surry, et al.; "Biaryl Phosphane Ligands in Palladium-Catalyzed Amination"; Angewandte Chemie Int'l Edition; vol. 47; Jan. 1, 2008; pp. 6338-6361.
Suzuki, et al.; "A New Hybrid Phosphine Ligand for Palladium-Catalyzed Amination of Aryl Halides"; Advanced Synthesis and Catalysis, 2008, vol. 350; pp. 652-656.
Grasa; et al.; "Amination Reactions of Aryl Halides with Nitrogen-Containing Reagents Mediated by Palladium/Imidazolium Salt Systems"; Journal of Organic Chemistry; vol. 66; 2001; pp. 7729-7737.
Souharce; et al.; "Amorphous Carbazole-based (Co)polymers for OFET Application"; Macromolecular Rapid Communications; vol. 30; 2009; pp. 1258-1262.
Watanabe, et al; "Palladium/P($t$-Bu)$_3$-catalyzed synthesis of $N$-aryl azoles and application to the synthesis of 4,4' ,4"-tris($N$—azolyl)triphenylamines"; Tetrahedron Letters; vol. 41, 2000; pp. 481-483.
Mann; et al; "Palladium-Catalyzed C-N(sp$^2$) Bond Formation: $N$-Arylation of Aromatic and Unsaturated Nitrogen and the Reductive Elimination Chemistry of Palladium Azolyl and Methyleneamido Complexes"; Journal of American Chemical Society; 1998; vol. 120 No. 4; pp. 827-828.
Old, et al.; "Efficient Palladium-Catalyzed $N$-Arylation of Indoles" Organic Letters; 2000; vol. 2 No. 10; pp. 1403-1406.
Hartwig, et al; "Room-Temperature Palladium-Catalyzed Amination of Aryl Bromides and Chlorides and Extended Scope of Aromatic C—N Bond Formation with a Commercial Ligand"; Journal of Organic Chemistry; 1999; vol. 64 No. 15; pp. 5575-5580.

* cited by examiner

*Primary Examiner* — Rita Desai
*Assistant Examiner* — Ben S Michelson
(74) *Attorney, Agent, or Firm* — Sughrue Mion, PLLC

(57) ABSTRACT

The present invention provides a process for effectively producing an N-(hetero)arylazole with high yield, which is useful as a medical or agrochemical product, an organic photoconductor material, an organic electroluminescent element material, or the like. The present invention relates to a process for producing an N-(hetero)arylazole, which includes reacting a (hetero)aryl (pseudo)halide with an NH-azole in the presence of: a catalyst including a palladium compound and a coordination compound; and a basic magnesium compound.

6 Claims, No Drawings

PROCESS FOR PRODUCING N-(HETERO)ARYLAZOLES

TECHNICAL FIELD

The present invention relates to a process for producing an N-(hetero)arylazole useful as a medical or agrochemical product, an organic photoconductor, an organic electroluminescent element material, or the like.

BACKGROUND ART

N-(hetero)arylazoles are compounds useful as medical or agrochemical products, organic photoconductors, organic electroluminescent element materials, and the like. These compounds have conventionally been produced by the Ullmann reaction, known as a process for synthesizing N-(hetero)arylamines, wherein a copper compound is used as a catalyst. The original Ullmann reaction involves such defects as use of a large amount of catalyst, harsh reaction conditions, limitation as to substrates, and complicated after-treatment, and has long been believed to be a reaction having poor usefulness. With the development of research in recent years, significant improvements are being made. However, there still remains the defect that a substrate which is highly reactive but is expensive, such as (hetero)aryl bromide, (hetero)aryl iodide, or (hetero)aryl boronic acid, is required.

With such background, an arylamination using a palladium compound as a catalyst (Buchwald-Hartwig amination) was developed in the 1990s. In comparison with the Ullmann reaction, this reaction uses a smaller amount of catalyst, reaction conditions for the reaction are milder, substrate generality is more extensive and, in addition, experimental procedures are comparatively easy. Further, even (hetero)aryl chlorides, which are inexpensive and readily available but which have been believed to be difficult to use due to their poor reactivity, becomes employable as the substrate by using an appropriate (i.e., electron-rich and bulky) coordination compound. Therefore, the reaction has attracted attention as a novel process for synthesizing N-(hetero)arylamines. Even now, fundamental investigations on the process are being made actively and, in addition, this reaction has come into wide use in the industrial production of chemical products (for example, Non-Patent Literature 1).

However, only a few reports have been made on application of the Buchwald-Hartwig amination to synthesis of N-(hetero)arylazoles (for example, Non-Patent Literature 2 to 7). Use of a base is necessary for this reaction, and alkali metal compounds are used in common as a base in these reports. Some of these reactions proceed under comparatively moderate conditions and permit use of (hetero)aryl chlorides (Non-Patent Literature 3, 4, 5, and 7). Additionally, regarding the Buchwald-Hartwig amination, the concept itself of using not an alkali metal compound but a magnesium compound as the base has long been proposed (Patent Literature 1).

On the other hand, there has been reported in recent years a reaction between indole which is one kind of NH-azoles and an aryl halide in which various magnesium compounds are used as bases in the presence of the catalyst composed of palladium(II) acetate and triphenylphosphine (Non-Patent Literature 8).

It has been reported very recently that, only when carbazole which is one kind of NH-azoles is used as a substrate, even by using a magnesium compound as a base, an intended N-arylcarbazole can be obtained in the presence of the catalyst composed of dichlorobis(triphenylphosphine)nickel(II) and triphenylphospnine (Non-Patent Literature 9).

CITATION LIST

Patent Literature

[Patent Literature 1] U.S. Pat. No. 5,576,460A

Non-Patent Literatures

[Non-Patent Literature 1] David S. Surry et al., Angewandte Chemie International Edition, 2008, 47, 6338-6361.

[Non-Patent Literature 2] Grace Mann et al., Journal of American Chemical Society, 1998, 120, 827-828.

[Non-Patent Literature 3] John F. Hartwig et al., The Journal of Organic Chemistry, 1999, 64, 5575-5580.

[Non-Patent Literature 4] David W. Old et al., Organic Letters, 2000, 2, 1403-1406.

[Non-Patent Literature 5] Makoto Watanabe et al., Tetrahedron Letters, 2000, 41, 481-483.

[Non-Patent Literature 6] Gabriela A. Grasa et al., The Journal of Organic Chemistry, 2001, 66, 7729-7737.

[Non-Patent Literature 7] Ken Suzuki et al., Advanced Synthesis and Catalysis, 2008, 350, 652-656.

[Non-Patent Literature 8] Benjamin S. Lane et al., Journal of American Chemical Society, 2005, 127, 8050-8057.

[Non-Patent Literature 9] Benjamin Souharce et al., Macromolecular Rapid Communications, 2009, 30, 1258-1262.

SUMMARY OF INVENTION

Technical Problem

The present invention has been made in consideration of the above-described circumstances, and an object thereof is to provide a process for effectively producing an N-(hetero)arylazole useful as, for example, a medical or agrochemical product, an organic photoconductor material, an organic electroluminescent element material, or the like.

Solution to Problem

With regard to the techniques described in Non-Patent Literatures 2 to 7, the catalysts are required to be used in a large amount of as much as 0.01 equivalent (1.0 mol %) or more as is different from the synthesis reaction of N-(hetero)arylamines which proceed with the aid of a slight amount of catalyst.

In the technique described in Patent Literature 1, with respect to reaction of NH-azoles, neither the concept nor specific examples thereof have been described at all.

In the reaction described in Non-Patent Literature 8, intended N-arylindoles cannot be obtained, while carbon atom adjacent to the nitrogen atom of indole reacts to produce C-arylindoles (the following reaction formula 1). Therefore, it has been considered that, in the case where a magnesium compound is used as a base instead of the alkali metal compound, it would be difficult to synthesize N-(hetero)arylazoles regioselectively.

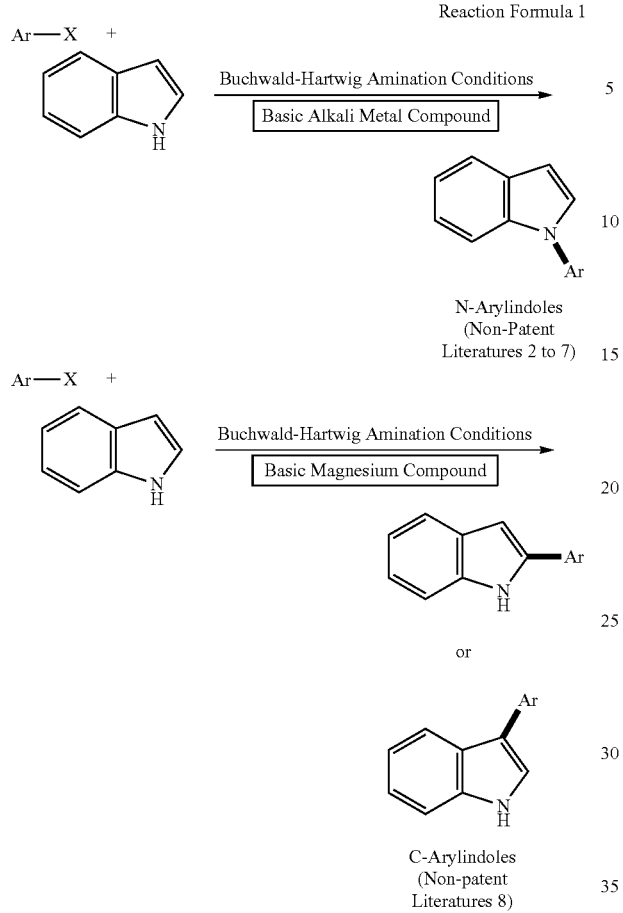

Reaction Formula 1

N-Arylindoles
(Non-Patent
Literatures 2 to 7)

C-Arylindoles
(Non-patent
Literatures 8)

With regard to the technique described in Non-Patent Literature 9, with this reaction, there remain problems that an inexpensive aryl chloride cannot be used as a substrate and that amount of the catalyst required is extremely large as much as 0.05 equivalent (5.0 mol %). That is, various problems with the synthesis of N-(hetero)arylazoles using the conventional Buchwald-Hartwig amination have not yet been solved by this report.

As a result of intensive investigations to solve the above-described problems, the inventors have found that, when a magnesium compound is used as a base upon reacting a (hetero)aryl halide with an NH-azole in the presence of a palladium catalyst, the amount of catalyst can be reduced markedly in comparison with the case of using an alkali metal compound as a base while keeping such advantages of the conventional processes (Non-Patent Literature 3, 4, 5, and 7). Further, it has also been found that, in the case where an appropriate (hetero)aryl halide is not readily available, it is possible to use a (hetero)aryl pseudohalide synthesized from a corresponding phenol derivative. Additionally, in the case of using a magnesium compound as a base in this reaction, there has been a fatal problem that intended N-(hetero)arylazoles cannot be obtained (Non-Patent Literature 8), but it has now been found that, even when a magnesium compound is used as a base, N-(hetero)arylazoles can be regioselectively obtained in the presence of an appropriate (i.e., electron-rich and bulky) coordination compound, thus the present invention having been completed based on these findings.

The present invention provides the following process for producing an N-(hetero)arylazole.

[1] A process for producing an N-(hetero)arylazole, which comprises reacting a (hetero)aryl (pseudo)halide with an NH-azole in the presence of: a catalyst comprising a palladium compound and a coordination compound; and a basic magnesium compound.

[2] The process according to [1], wherein the coordination compound is at least one compound selected from the group consisting of:

monophosphines represented by the following general formula (1)

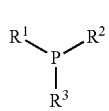

(1)

wherein P represents a phosphorus atom, $R^1$ and $R^2$ each independently represents an alkyl group, and $R^3$ represents a hydrocarbyl group which may have a substituent, a heteroaryl group which may have a substituent or a ferrocenyl group which may have a substituent;

diphosphines represented by the following general formula (2)

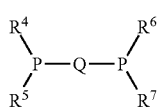

(2)

wherein P represents a phosphorus atom, $R^4$ to $R^7$ each independently represents an alkyl group, or an aryl group which may have a substituent, and Q represents a divalent group which may have a substituent;

(benzo)imidazol-ylidenes represented by the following general formula (3-1) or (3-2)

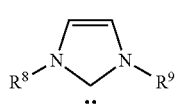

(3-1)

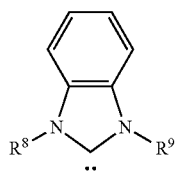

(3-2)

wherein N represents a nitrogen atom, $R^8$ and $R^9$ each independently represents an alkyl group; and imidazolidin-ylidenes represented by the following general formula (4)

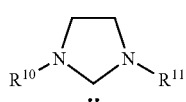

(4)

wherein N represents a nitrogen atom, and $R^{10}$ and $R^{11}$ each independently represents an alkyl group or an aryl group.

[3] The process according to [1] or [2], wherein the (hetero)aryl (pseudo)halide is a compound represented by the following general formula (5)

(5)

wherein (Het)Ar represents an aromatic ring group which may have a substituent or a heteroaromatic ring group which may have a substituent, X represents a (pseudo)halogeno group, a subscript n of X represents the number of the substituent X into (Het)Ar, and is an integer of from 1 to 7.

[4] The process according to [3], wherein X in the compound represented by the general formula (5) is a chloro group, a bromo group, a (halo)alkanesulfonyloxy group or an arenesulfonyloxy group, and n is an integer of from 1 to 3.

[5] The process according to any one of [1] to [4], wherein the NH-azole is at least one compound selected from the group consisting of 1H-pyrrole which may have a substituent, indole which may have a substituent, carbazole which may have a substituent, benzocarbazoles which may have a substituent, dibenzocarbazoles which may have a substituent, indolocarbazoles which may have a substituent, biindoles which may have a substituent and bicarbazoles which may have a substituent.

[6] The process according to any one of [1] to [5], wherein the basic magnesium compound is at least one kind selected from the group consisting of: inorganic basic magnesium compounds; and organic basic magnesium compounds represented by the following general formula (6):

(6)

wherein Mg represents a magnesium atom; $R^{12}$ and $R^{13}$ each independently represents a hydrocarbyl group, an alkoxy group, an amino group or a halogeno group; and when $R^{12}$ represents a halogeno group, $R^{13}$ do not represent a halogeno group; and when $R^{13}$ represents a halogeno group, $R^{12}$ do not represent a halogeno group.

[7] The process according to any one of [1] to [6], wherein the basic magnesium compound is a Grignard reagent.

Advantageous Effects of the Invention

According to the production process of the present invention, N-(hetero)arylazoles useful as medical or agrochemical products, organic photoconductor materials, organic electroluminescent element materials, or the like can be produced with low cost and high efficiency.

DESCRIPTION OF EMBODIMENTS

The production process of the present invention will be described in detail below.

Palladium compounds to be used in the production process of the invention are not particularly limited, but preferred examples thereof include bis(dibenzylideneacetone)palladium(0), tris(dibenzylideneacetone)dipalladium(0), tris(dibenzylideneacetone)dipalladium(0)-chloroform adduct, palladium(II) chloride, palladium(II) bromide, dichlorobis(acetonitrile)palladium(II), dichlorobis(benzonitrile)palladium(II), dichloro(1,5-cyclooctadiene)palladium(II), palladium(II) acetate, allylpalladium(II) chloride dimer, methallylpalladium(II) chloride dimer, crotylpalladium(II) chloride dimer, and cinnamylpalladium(II) chloride dimer.

These palladium compounds in the production process of the invention may be used independently or in a proper combination of two or more thereof. The amount of the palladium compound is not particularly limited, but is usually from 0.00001 to 0.1 equivalents (from 0.001 to 10.0 mol %) in terms of palladium atom, per mol of the NH-azoles and, in view of profitability and reaction reproducibility, a proper amount is selected preferably within the range of from 0.0001 to 0.05 equivalents (0.01 to 5.0 mol %).

In view of catalyst activity and regioselectivity of the reaction, the coordination compound to be used in the production process of the invention is preferably selected from the group consisting of:

monophosphines represented by the following general formula (1):

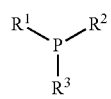

(1)

(wherein P represents a phosphorus atom, $R^1$ and $R^2$ each independently represents an alkyl group, and $R^3$ represents a hydrocarbyl group which may have a substituent, a heteroaryl group which may have a substituent, or a ferrocenyl group which may have a substituent);

diphosphines represented by the following general formula (2):

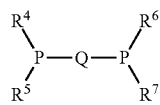

(2)

(wherein P represents a phosphorus atom, $R^4$ to $R^7$ each independently represents an alkyl group or an aryl group which may have a substituent, and Q represents a divalent group which may have a substituent);

(benzo)imidazol-ylidenes represented by the following general formula (3-1) or (3-2):

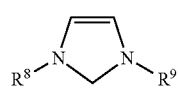

(3-1)

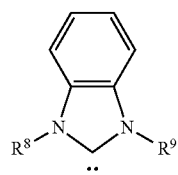

(3-2)

(wherein N represents a nitrogen atom, and $R^8$ and $R^9$ each independently represents an alkyl group); and imidazolidin-ylidenes represented by the following general formula (4):

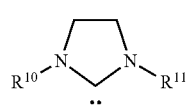

(4)

(wherein N represents a nitrogen atom, and $R^{10}$ and $R^{11}$ each independently represents an alkyl group or an aryl group).

In the monophosphines represented by the general formula (1), $R^1$ and $R^2$ each independently represents an alkyl group. Examples of the alkyl group include alkyl groups containing preferably from 1 to 20 carbon atoms, more preferably from 2 to 15 carbon atoms, further more preferably from 3 to 10 carbon atoms, which may be straight, branched, or cyclic. Of these, a secondary alkyl group, a tertiary alkyl group, or a cycloalkyl group is particularly preferred. Specific examples thereof include an isopropyl group, a tert-butyl group, a cyclohexyl group, and a 1-adamantyl group. Additionally, $R^1$ and $R^2$ may be connected to each other to form a ring containing the phosphorus atom. $R^3$ represents a hydrocarbyl group which may have a substituent, a heteroaryl group which may have a substituent, or a ferrocenyl group which may have a substituent. Additionally, $R^3$ and $R^1$, or $R^3$ and $R^2$ may be connected to each other to form a ring containing the phosphorus atom.

Specific preferable examples of the monophosphines represented by the general formula (1) include tri-tert-butylphosphine ($^tBu_3P$), di-tert-butylmethylphosphine ($^tBu_2PMe$), di-tert-butylneopentylphosphine (DTBNpP), triisopropylphosphine ($^iPr_3P$), tricyclohexylphosphine ($Cy_3P$), dicyclohexyl(2,4,6-trimethylphenyl)phosphine ($Cy_2PMes$), 1-[2-(di-tert-butylphosphino)phenyl]-3,5-diphenyl-1H-pyrazole (TrippyPhos), 5-(di-tert-butylphosphino)-1',3',5'-triphenyl-1'H-[1,4']bipyrazole (BippyPhos), [4-(N,N-dimethylamino)phenyl]di-tert-butylphosphine (A-$^{ta}$phos), [4-(N,N-dimethylamino)phenyl]dicyclohexylphosphine (A-$^{ca}$phos), (2-biphenyl)di-tert-butylphosphine (JohnPhos), (2-biphenyl)dicyclohexylphosphine (Cy-JohnPhos), 2-di-tert-butylphosphino-2',4',6'-triisopropylbiphenyl (tBuXPhos), 2-dicyclohexylphosphino-2',6'-diisopropoxybiphenyl (RuPhos), 2-dicyclohexylphosphino-2',6'-dimethoxybiphenyl (SPhos), 2-dicyclohexylphosphino-2'-(N,N-dimethylamino)biphenyl (DavePhos), 2-di-tert-butylphosphino-2'-(N,N-dimethylamino)biphenyl (tBuDavePhos), 2-dicyclohexylphosphino-2',4',6'-triisopropylbiphenyl (XPhos), 2-(dicyclohexylphosphino)-3,6-dimethoxy-2',4',6'-triisopropyl-1,1'-biphenyl (BrettPhos), 2-(di-tert-butylphosphino)-3,6-dimethoxy-2',4',6'-triisopropyl-1,1'-biphenyl (tBuBrettPhos), 2'-(dicyclohexylphosphino)acetophenone ethylene ketal (Symphos), 1,2,3,4,5-pentaphenyl-1'-(di-tert-butylphosphino)ferrocene (Q-Phos), di(1-adamantyl)-n-butylphosphine (cataCXium A), di(1-adamantyl)benzylphosphine (cataCXium ABn), 2-(dicyclohexylphosphino)-1-phenyl-1H-pyrrole (cataCXium PCy), 2-(dicyclohexylphosphino)-1-phenylindole (cataCXium PInCy), 2-(di-tert-butylphosphino)-1-phenylindole (cataCXium PIntB), 2-(di-tert-butylphosphino)-1-phenyl-1H-pyrrole (cataCXium PtB), N-methyl-2-(2-dicyclohexylphosphinophenyl)indole (CM-Phos), N-[2-di(1-adamantyl)phosphinophenyl]morpholine (Mor-DarPhos), 3-tert-butyl-4-(2,6-dimethoxyphenyl)-2,3-dihydrobenzo[d][1,3]oxaphosphole (BI-DIME), di-tert-butyl(2,2-diphenyl-1-methylvinyl)phosphine (vBRIDP), dicyclohexyl(2,2-diphenyl-1-methylvinyl)phosphine (Cy-vBRIDP), di-tert-butyl(2,2-diphenyl-1-methyl-1-cyclopropyl)phosphine (cBRIDP), and dicyclohexyl(2,2-diphenyl-1-methyl-1-cyclopropyl)phosphine (Cy-cBRIDP), whose structural formulae are shown below.

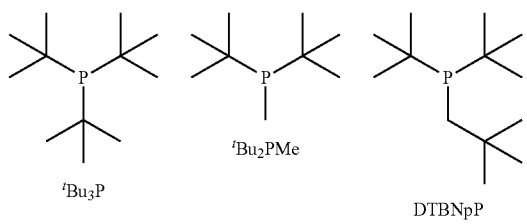

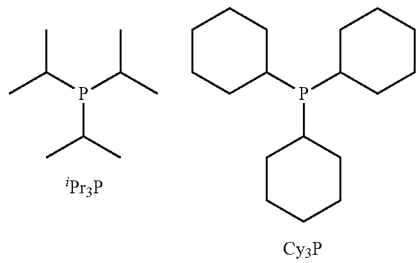

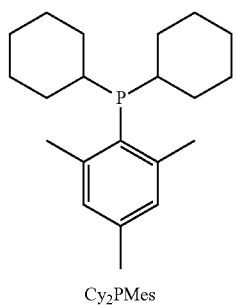

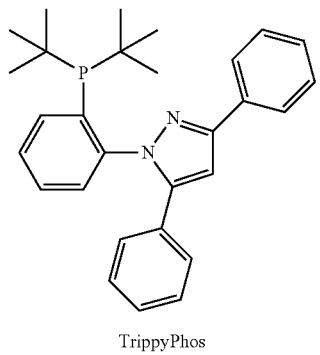

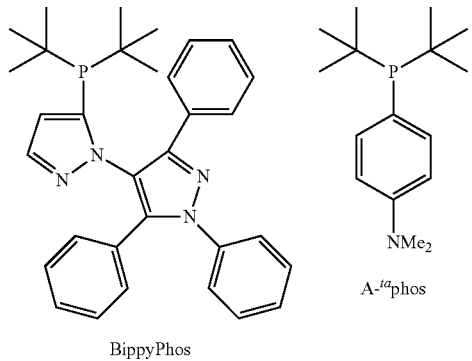

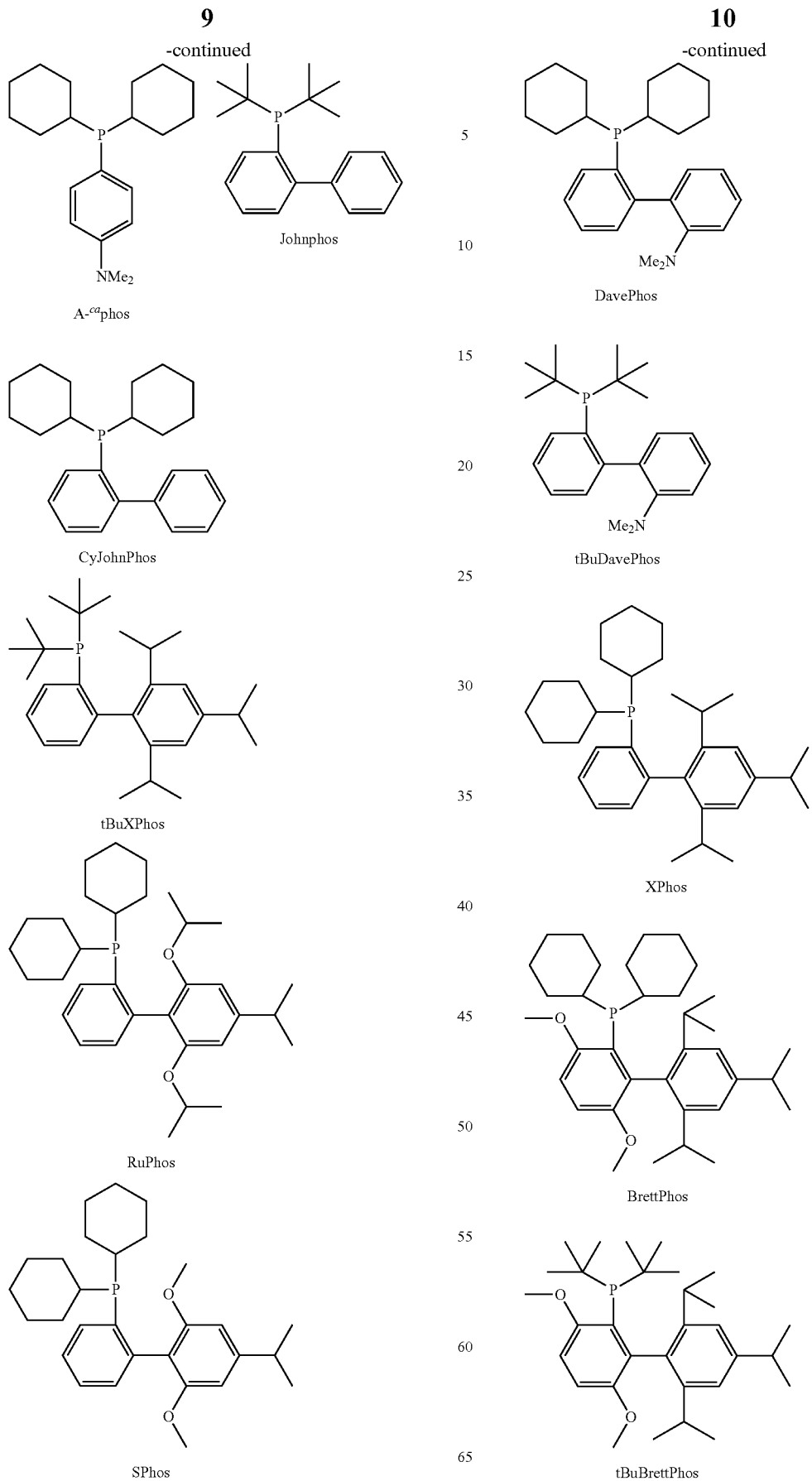

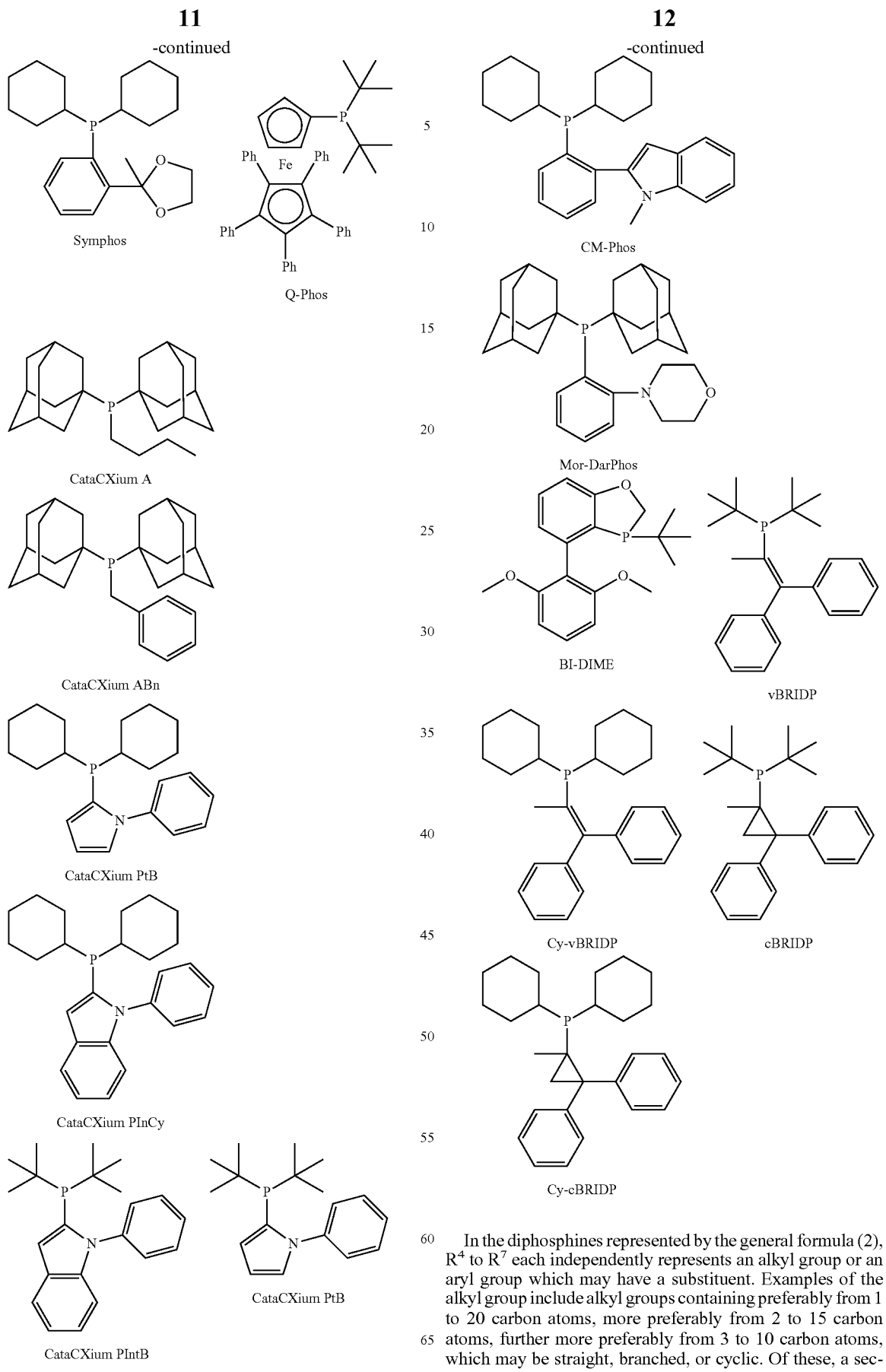

In the diphosphines represented by the general formula (2), $R^4$ to $R^7$ each independently represents an alkyl group or an aryl group which may have a substituent. Examples of the alkyl group include alkyl groups containing preferably from 1 to 20 carbon atoms, more preferably from 2 to 15 carbon atoms, further more preferably from 3 to 10 carbon atoms, which may be straight, branched, or cyclic. Of these, a secondary alkyl group, a tertiary alkyl group, or a cycloalkyl group is particularly preferred. Specific examples thereof include an isopropyl group, a tert-butyl group, a cyclohexyl group, and a 1-adamantyl group. Examples of the aryl group include aryl groups containing preferably from 6 to 18 carbon atoms, more preferably from 6 to 12 carbon atoms. Specific examples thereof include a phenyl group, a methylphenyl group, a dimethylphenyl group, a naphthyl group, and a biphenyl group. Additionally, $R^4$ and $R^5$, and $R^6$ and $R^7$ each may be connected to each other to form a ring containing the phosphorus atom. Q represents a divalent group which may have a substituent. In view of catalyst activity and regioselectivity of the reaction, examples of the divalent group include those divalent groups which give a phosphorus atom-transition metal atom-phosphorus atom angle (∠PMP) in a transition metal diphosphine complex represented by the following general formula (7), that is, a bite angle in the diphosphine, of 75 to 140°, preferably 80 to 130°, more preferably 85 to 120°.

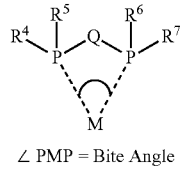

(7)

∠ PMP = Bite Angle (wherein P represents a phosphorus atom, $R^4$ to $R^7$ each independently represents an alkyl group or an aryl group which may have a substituent, Q represents a divalent group which may have a substituent, and M represents a transition metal atom).

Specific examples of the diphosphines represented by the general formula (2) include 1,1'-bis(diisopropylphosphino)ferrocene (DiPPF), 1,1'-bis(dicyclohexylphosphino)ferrocene (DCyPF), 1-[2-(dicyclohexylphosphino)ferrocenyl]ethyl-di-tert-butylphosphine (CyPF-tBu), 1,1'-bis(di-tert-butylphosphino)ferrocene (DtBPF), 1,1'-bis(diphenylphosphino)ferrocene (DPPF), 9,9-dimethyl-4,5-bis(di-tert-butylphosphino)xanthene (tBuXantphos), 4,5-bis(diphenylphosphino)-9,9-dimethylxanthene (Xantphos), (oxydi-2,1-phenylene)bis(diphenylphosphine) (DPEPhos), and 2,2'-bis(diphenylphosphino)-1,1'-binaphthyl (BINAP), whose structural formulae are shown below.

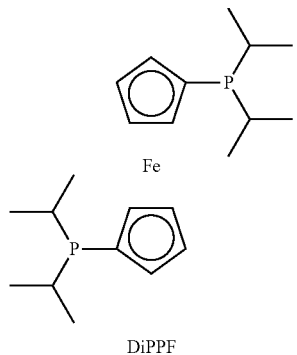

DiPPF

-continued

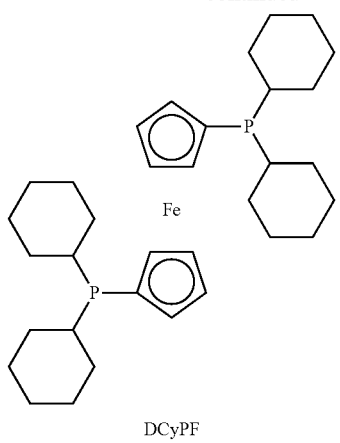

DCyPF

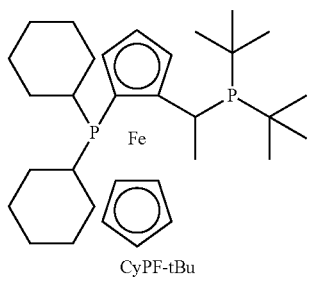

CyPF-tBu

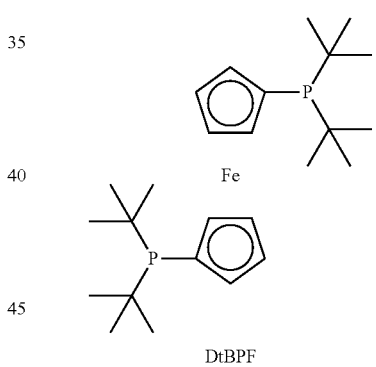

DtBPF

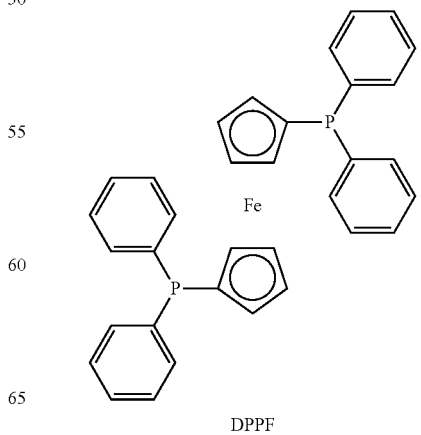

DPPF

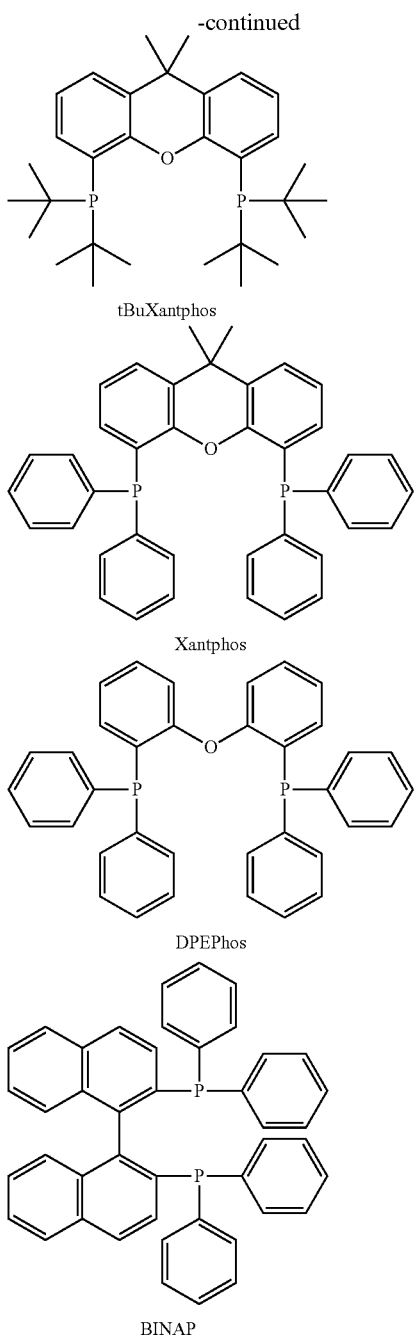

tBuXantphos

Xantphos

DPEPhos

BINAP

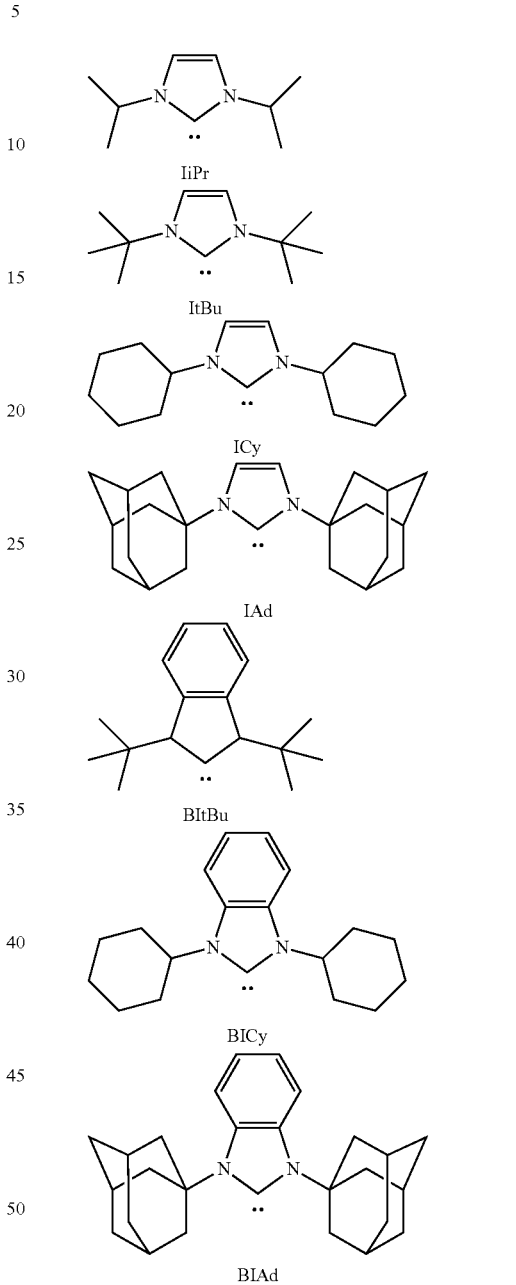

IiPr

ItBu

ICy

IAd

BItBu

BICy

BIAd dazol-2-ylidene (IAd), 1,3-di-tert-butylbenzimidazol-2-ylidene (BItBu), 1,3-dicyclohexylbenzimidazol-2-ylidene (BICy), and 1,3-di(1-adamantyl)imidazol-2-ylidene (BIAd), whose structural formulae are shown below.

In the (benzo)imidazol-ylidenes represented by the general formula (3-1) or (3-2), $R^8$ and $R^9$ each independently represents an alkyl group. Examples of the alkyl group include alkyl groups containing preferably from 1 to 20 carbon atoms, more preferably from 2 to 15 carbon atoms, further more preferably from 3 to 10 carbon atoms, which may be straight, branched, or cyclic. Of these, a secondary alkyl group, a tertiary alkyl group, or a cycloalkyl group is particularly preferred. Specific examples thereof include an isopropyl group, a tert-butyl group, a cyclohexyl group, and a 1-adamantyl group. Particularly preferred specific examples of the (benzo)imidazol-ylidenes represented by the general formula (3-1) or (3-2) include 1,3-diisopropylimidazol-2-ylidene (IiPr), 1,3-di-tert-butylimidazol-2-ylidene (ItBu), 1,3-dicyclohexylimidazol-2-ylidene (ICy), 1,3-di(1-adamantyl)imi- In the imidazolidin-ylidenes represented by the general formula (4), $R^{10}$ and $R^{11}$ each independently represents an alkyl group or an aryl group. Examples of the alkyl group include alkyl groups containing preferably from 1 to 20 carbon atoms, more preferably from 2 to 15 carbon atoms, further more preferably from 3 to 10 carbon atoms, which may be straight, branched, or cyclic. Of these, a secondary alkyl group, a tertiary alkyl group, or a cycloalkyl group is particularly preferred. Specific examples thereof include an isopropyl group, a tert-butyl group, a cyclohexyl group, and a 1-adamantyl group. Examples of the aryl group include aryl groups containing preferably from 6 to 18 carbon atoms, more preferably from 6 to 12 carbon atoms. Specific examples thereof include a phenyl group, a 2,6-dimethylphenyl group, a 2,4,6-trimethylphenyl group, and a 2,6-diisopropylphenyl group.

Specific examples of particularly preferred imidazolidin-ylidenes represented by the general formula (4) include 1,3-diisopropylimidazolidin-2-ylidene (SIiPr), 1,3-dicyclohexy-limidazolidin-2-ylidene (SICy), 1,3-di(1-adamantyl) imidazolidin-2-ylidene (SIAd), 1,3-bis(2,6-diisopropylphenyl)imidazolidin-2-ylidene (SIPr), and 1,3-bis(2,4,6-trimethylphenyl)imidazolidin-2-ylidene (SIMes), whose structural formulae are shown below.

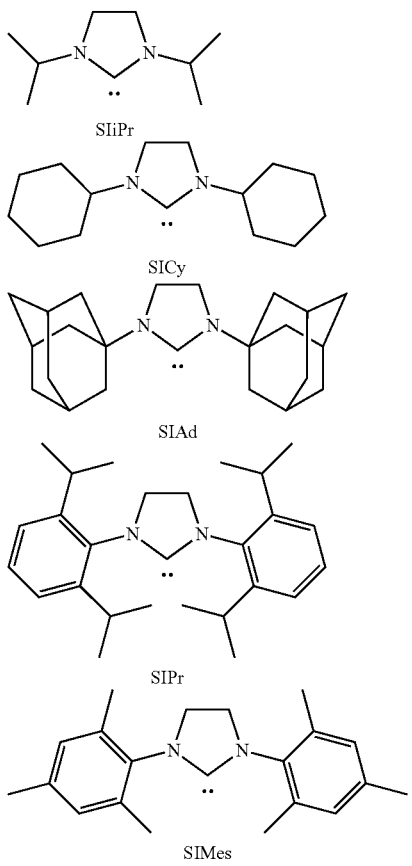

In the case where the coordination compound to be used in the production process of the invention is unstable in the air, it is also preferred to use, as a substitute therefor, a salt of the coordination compound obtained by reacting with a Broensted acid. Specific examples of preferred Broensted acid include hydrogen chloride, hydrogen bromide, hydrogen iodide, tetrafluoroboric acid, and tetraphenylboric acid. Specific examples of the salt of coordination compound include tri-tert-butylphosphonium tetrafluoroborate ($^{t}Bu_3PHBF_4$), tri-tert-butylphosphonium tetraphenylborate ($^{t}Bu_3PHBPh_4$), di-tert-butylmethylphosphonium tetrafluoroborate ($^{t}Bu_2PMeHBF_4$), di-tert-butylneopentylphosphonium tetrafluoroborate (DTBNpPHBF$_4$), tricyclohexylphosphonium tetrafluoroborate (Cy$_3$PHBF$_4$), di(1-adamantyl)-n-butylphosphonium iodide (cataCXium AHI), (9-butyl-9-flouorenyl)dicyclohexylphosphonium tetrafluoroborate (cataCXium FBu), dicylclohexyl[9-(3-phenylpropyl)-9-fluorenyl]phosphonium tetrafluoroborate (cataCXium FPrPh), 1,3-diisopropylimidazolium tetrafluoroborate (IiPrHBF$_4$), 1,3-di-tert-butylimidazolium tetrafluoroborate (ItBuHBF$_4$), 1,3-dicyclohexylimidazolium chloride (ICy-HCl), 1,3-di(1-adamantyl)imidazolium tetrafluoroborate (IAdHBF$_4$), 1,3-diisopropylimidazolinium tetrafluoroborate (SIiPrHBF$_4$), 1,3-dicyclohexylimidazolinium chloride (SICyHCl), 1,3-di(1-adamantyl)imidazolinium tetrafluoroborate (SIAdHBF$_4$), 1,3-bis(2,6-diisopropylphenyl)imidazolinium chloride (SIPrHCl), and 1,3-bis(2,4,6-trimethylphenyl)imidazolinium chloride (SIMesHCl).

These coordination compounds in the production process of the invention may be used independently or in a proper combination of two or more thereof. The amount of the coordination compound to be used is not particularly limited, but is usually properly selected within the range of from 0.5 to 10.0 equivalents, preferably from 0.8 to 5.0 equivalents, per mol of palladium atom in the palladium compound.

Additionally, in the production process of the invention, method of adding the catalyst including the palladium compound and the coordination compound is not particularly limited, but the palladium compound and the coordination compound may be independently added to the reaction system; a catalyst solution previously prepared by reacting the palladium compound and the coordination compound with each other outside the reaction system may be added; or they may be added as a palladium complex synthesized by the reaction between the palladium compound and the coordination compound.

Specific examples of such palladium complex include acetato(2'-di-tert-butylphosphino-1,1'-biphenyl-2-yl)palladium(II) (Pd(OAc)(johnphos)), allylchloro[1,3-bis(2,6-diisopropylphenyl)imidazolidin-2-ylidene]palladium(II) (PdCl(π-alllyl)(SIPr)), allylchloro(di-tert-butylneopentylphosphine)palladium(II) (PdCl(π-allyl)(DTBNpP)), bis(di-tert-butylneopentylphosphine)palladium(0) (Pd(DTBNpP)$_2$), bis(tri-tert-butylphosphine)palladium(0) (Pd($^{t}Bu_3$P)$_2$), chloro(2-dicyclohexylphosphino-2',4',6'-triisopropyl-1,1'-biphenyl)[2-(2-aminoethyl)phenyl]pallaldium(II) (PdCl(bpa)(xphos)), chloro[(1,2,3-η)-3-phenyl-2-propenyl]-[1,3-bis(2,6-diisopropylphenyl)imidazolidin-2-ylidene]-palladium(II) (PdCl(π-cinnamyl)(SIPr)), di-μ-bromobis(tri-tert-butylphosphine)dipalladium(I) ([PdBr($^{t}Bu_3$P)]$_2$), bis[di-tert-butyl(4-dimethylaminophenyl)phosphine] dichloropalladium(II) (PdCl$_2$(a-$^{ta}$phos)$_2$), bis[dicyclohexyl (4-dimethylaminophenyl)phosphine]dichloropalladium(II) (PdCl$_2$(a-$^{ta}$phos)$_2$), [1,1'-bis(di-tert-buty lphosphino)ferrocene]dichloropalladium(II) (PdCl$_2$(DtBPF)), bis[dicyclohexyl(2,2-diphenyl-1-methylvinyl)phosphine]dichloropalladium(II) (PdCl$_2$(cy-vbridp)$_2$), [di-tert-butyl(2,2-diphenyl-1-methyl-1-cyclopropyl)phosphine]dichloropalladium(II) (PdCl$_2$(cbridp)), and allylchloro[di-tert-butyl(2,2-diphenyl-1-methyl-1-cyclopropyl)phosphine]palladium(II) (PdCl(π-allyl)(cbridp)), whose structural formulae are shown below.

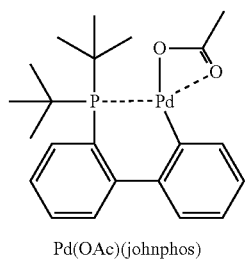

Pd(OAc)(johnphos)

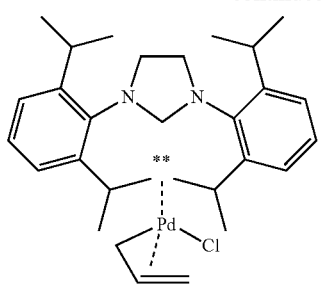
PdCl(π-allyl)(SIPr)
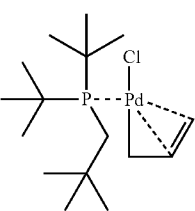
PdCl(π-allyl)(DTBNpP)
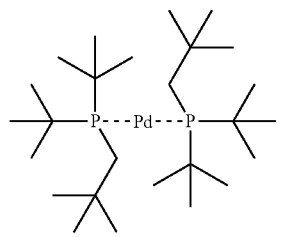
Pd(DTBNpP)$_2$
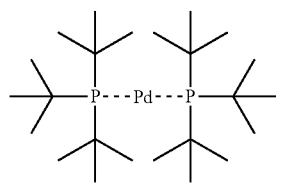
Pd($^t$Bu$_3$P)$_2$
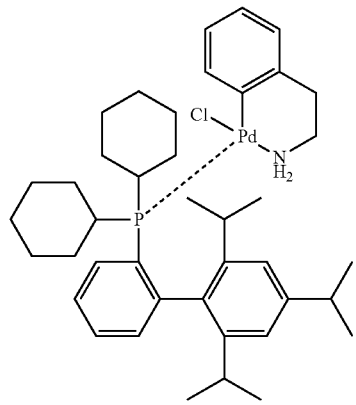
PdCl(bpa)(xphos)
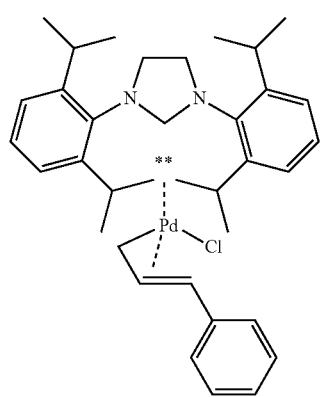
PdCl(π-cinnamyl)SIPr
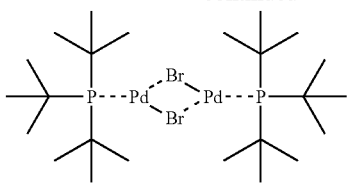
[PdBr($^t$Bu$_3$P)]$_2$
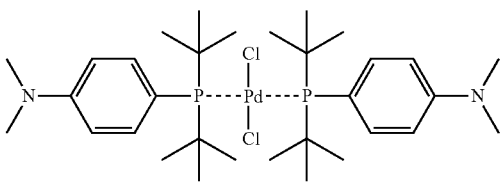
PdCl$_2$(a-$^{ta}$phos)$_2$
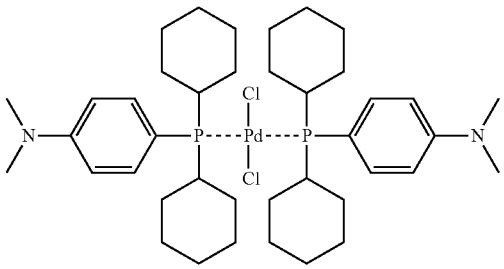
PdCl$_2$(a-$^{ca}$phos)$_2$
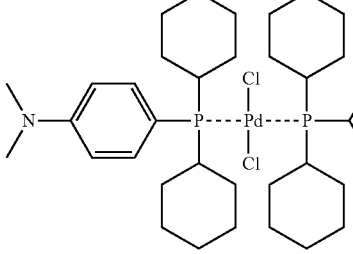
PdCl$_2$(DtBPF)
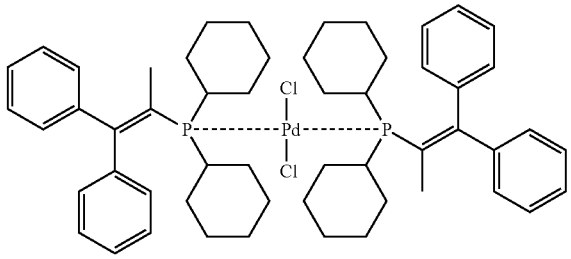
PdCl$_2$(cy-vbridp)$_2$

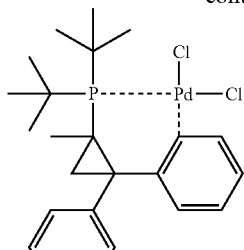

PdCl₂(cbridp)

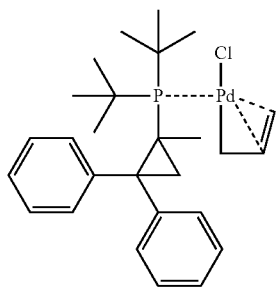

PdCl(π-allyl)cbridp)

These palladium complexes in the production process of the invention may be used independently or in a proper combination of two or more thereof. In addition, the palladium complexes may be used in a proper combination with the coordination compounds in the production process of the invention.

The (hetero)aryl (pseudo)halide to be used in the production process of the invention is preferably a compound represented by the following general formula (5):

(Het)Ar—X$_n$     (5)

(wherein (Het)Ar represents an aromatic ring group which may have a substituent or a heteroaromatic ring group which may have a substituent, X represents a (pseudo)halogeno group, and a subscript n of X represents the number of the substituent X into (Het)Ar, and is an integer of from 1 to 7).

In the compounds represented by the general formula (5), (Het)Ar represents an aromatic ring group which may have a substituent or a heteroaromatic ring group which may have a substituent. The aromatic ring group is not particularly limited, but examples thereof include those groups which are derived from aromatic rings containing preferably from 6 to 30 carbon atoms, more preferably from 6 to 25 carbon atoms, further more preferably from 6 to 20 carbon atoms. Specific examples of particularly preferred aromatic ring include benzene, naphthalene, anthracene, phenanthrene, pyrene, perylene, and fluorene, whose structural formulae are shown below. A dimer may be formed by these aromatic rings, and specific examples thereof include biphenyl, 1,1'-binaphthyl, 9,9'-bianthryl, and 9,9'-spirobi[9H-fluorene]. Further, these aromatic ring groups may be substituted by an oxo group, and specific examples thereof include anthraquinone and fluorenone.

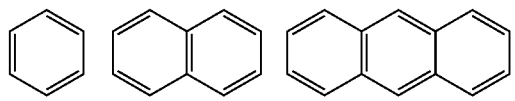

Benzene     Naphthalene     Anthracene

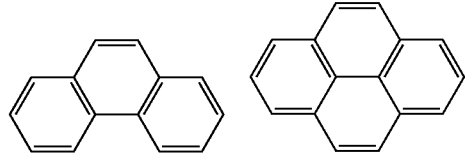

Phenanthrene     Pylene

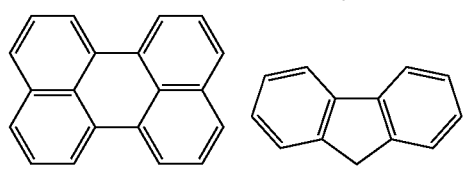

Perylene     9H-Fluorene

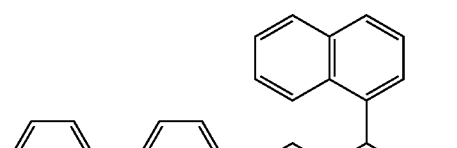

Biphenyl     1,1'-Binaphthyl

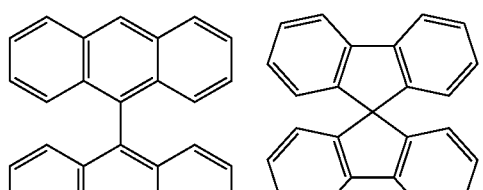

9,9'-Bianthryl     9,9'-Spirobi[9H-fluorene]

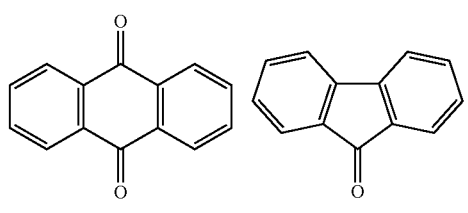

Anthraquinone     Fluorenone

The heteroaromatic ring group is not particularly limited, but examples thereof include those groups which are derived from heteroaromatic rings containing preferably from 1 to 25 carbon atoms, more preferably from 1 to 20 carbon atoms, further more preferably from 2 to 15 carbon atoms. Specific examples of particularly preferred heteroaromatic ring include furan, thiophene, 1H-pyrrole, pyridine, 1,3,4-oxadiazole, 1,3,4-thiadiazole, 1,3,5-triazine, benzofuran, dibenzofuran, benzothiophene, dibenzothiophene, indole, carbazole, quinoline, acridine, phenanthridine, benzo[f]quinoline, benzo[g]quinoline, benzo[h]quinoline, isoquinoline, benzo[f]isoquinoline, benzo[g]isoquinoline, and benzo[h]isoquinoline, whose structural formulae are shown below.

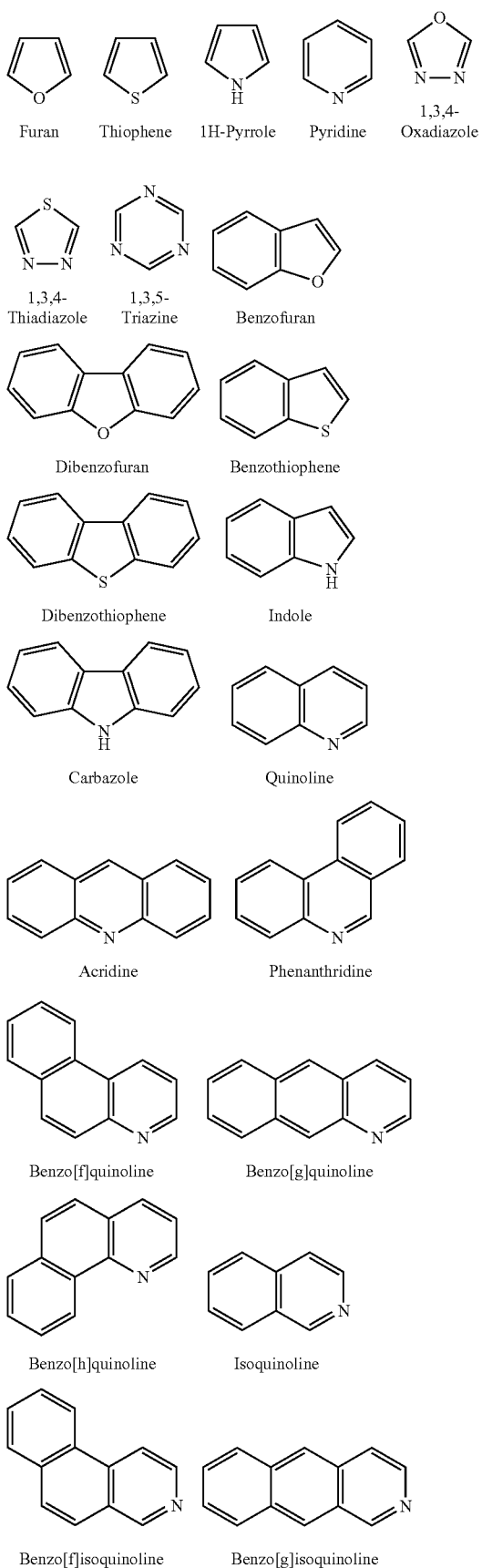

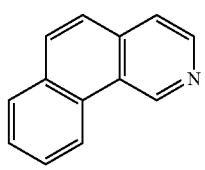

Benzo[h]isoquinoline

In the compounds represented by the general formula (5), X represents a (pseudo)halogeno group which means pseudohalogeno group and/or halogeno group, and preferred examples thereof include a chloro group, a bromo group, a (halo)alkanesulfonyloxy group, and an arenesulfonyloxy group. Specific examples of the (halo)alkanesulfonyloxy group include a methanesulfonyloxy group, a trifluoromethanesulfonyloxy group, and a nonafluorobutanesulfonyloxy group, and examples of the arenesulfonyloxy group include a benzenesulfonyloxy group and a p-toluenesulfonyloxy group. In view of reactivity, a trifluoromethanesulfonyloxy group is preferred and, in view of economic efficiency, a p-toluenesulfonyloxy group is preferred. A subscript n of X represents the number of the substituent X into (Het)Ar, and is an integer of from 1 to 7, preferably from 1 to 5, more preferably from 1 to 3. In the case where n is 2 or more, that is, in the case where (Het)Ar is substituted by plural Xs, all of the plural Xs may be the same, or they may be independently different from each other.

The NH-azole to be used in the production process of the invention is a nitrogen-containing-5-membered heteroaryl compound having a hydrogen atom on the nitrogen atom, and specific examples thereof include 1H-pyrrole, pyrazole, imidazole, 1,2,3-triazole, 1,2,4-triazole, and tetrazole, whose structural formulae are shown below. These NH-azoles may form a fused ring together with themselves or aromatic rings, and specific examples thereof include indole, isoindole, indazole, benzimidazole, benzotriazole, carbazole, 7H-benzo[c]carbazole, 7H-dibenzo[c,g]carbazole, indolo[2,3-a]carbazole, and indolo[3,2-b]carbazole. Further, a dimer may be formed by these compounds, and specific examples thereof include 3,3'-bi[1H-indole], 5,5'-bi[1H-indole], 3,3'-bi[9H-carbazole], 1,9'-bi[9H-carbazole], and 3,9'-bi[9H-carbazole].

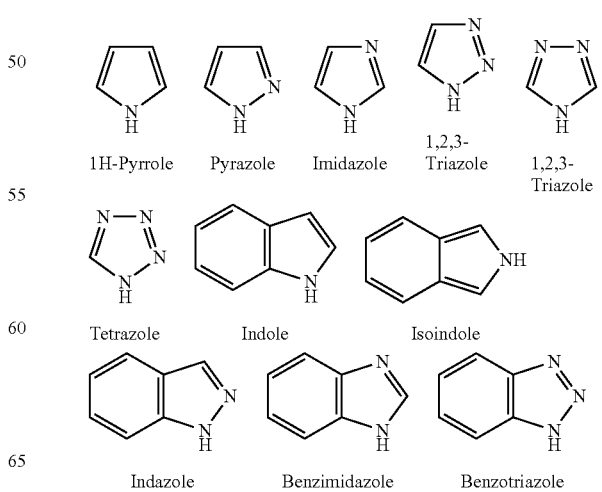

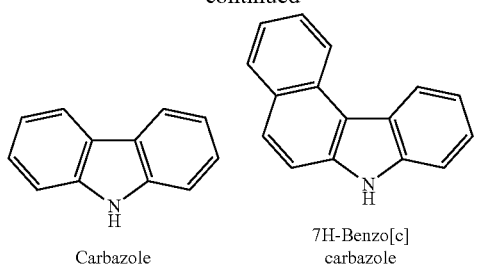

Carbazole

7H-Benzo[c]carbazole

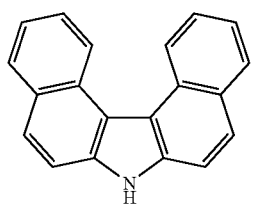

7H-Dibenzo[c,g]carbazole

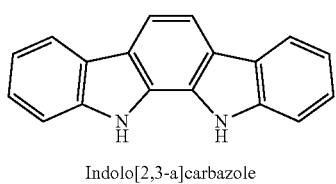

Indolo[2,3-a]carbazole

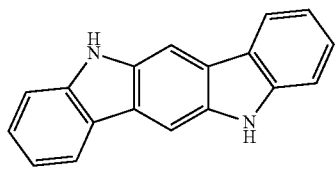

Indolo[3,2-b]carbazole

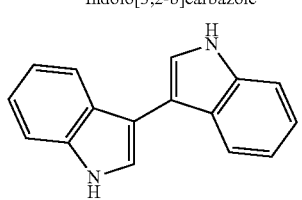

3,3'-Bi[1H-indole]

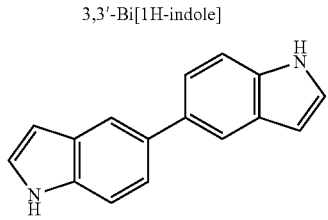

5,5'-Bi[1H-indole]

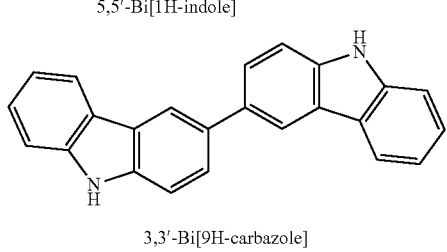

3,3'-Bi[9H-carbazole]

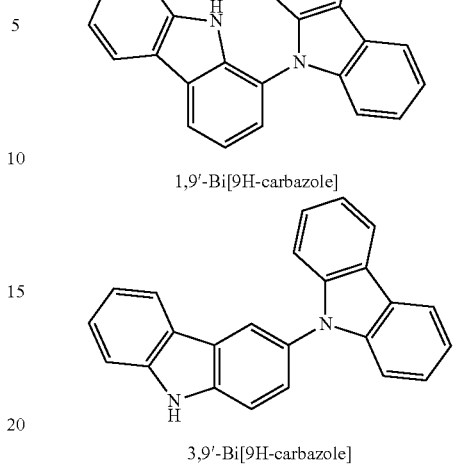

1,9'-Bi[9H-carbazole]

3,9'-Bi[9H-carbazole]

Particularly preferred examples of the NH-azole include 1H-pyrrole, indole, carbazole, benzocarbazoles, dibenzocarbazoles, indolocarbazoles, biindoles, and bicarbazoles.

The (hetero)aryl (pseudo)halide and the NH-azole to be used in the production process of the invention may have a substituent. The substituent is not particularly limited as long as it does not participate in the reaction in the production process of the invention, and examples thereof include a hydrocarbyl group, an aliphatic heterocyclic group, a heteroaryl group, an alkoxy group, an aryloxy group, an aralkyloxy group, a heteroaryloxy group, an acyloxy group, a carbonate group, an acyl group, a carboxyl group, an alkoxycarbonyl group, an aryloxycarbonyl group, an aralkyloxycarbonyl group, a heteroaryloxycarbonyl group, a carbamoyl group, a hydroxamic acid group, an alkylthio group, an arylthio group, an aralkylthio group, a heteroarylthio group, an acylthio group, an alkoxycarbonylthio group, a sulfinyl group, a sulfino group, a sulfenamoyl group, a sulfonyl group, a sulfo group, a sulfamoyl group, an amino group, a hydrazino group, an ureido group, a nitro group, a phosphino group, a phosphinyl group, a phosphinico group, a phosphono group, a silyl group, a boryl group, a cyano group, and a fluoro group; and preferable examples thereof include a hydrocarbyl group, an alkoxy group, an aryloxy group, an acyl group, an alkylthio group, an arylthio group, an amino group, a silyl group, a cyano group, and a fluoro group.

Preferred substituents will be described in more detail. As the hydrocarbyl group, examples thereof include an alkyl group, an alkenyl group, an alkynyl group, an aryl group, and an aralkyl group. Of these, examples of the alkyl group includes alkyl groups containing preferably from 1 to 15 carbon atoms, more preferably from 1 to 12 carbon atoms, further more preferably from 1 to 8 carbon atoms, which may be straight, branched, or cyclic. Specific examples thereof include a methyl group, an ethyl group, a n-propyl group, an isopropyl group, a cyclopropyl group, a n-butyl group, a 2-butyl group, an isobutyl group, a tert-butyl group, a cyclobutyl group, a n-pentyl group, a 2-pentyl group, a tert-pentyl group, a 2-methylbutyl group, a 3-methylbutyl group, a 2,2-dimethylpropyl group, a cyclopentyl group, a n-hexyl group, a 2-hexyl group, a 3-hexyl group, a tert-hexyl group, a 2-methylpentyl group, a 3-methylpentyl group, a 4-methylpentyl group, a 2-methylpentan-3-yl group, a cyclohexyl group, a n-heptyl group, and a n-octyl group. As the alkenyl group, examples thereof include alkenyl groups containing preferably from 2 to 15 carbon atoms, more preferably from 2 to 12 carbon atoms, further more preferably from 2 to 8 carbon atoms, which may be straight, branched, or cyclic. Specific examples thereof include a vinyl group, a propenyl group, a butenyl group, a pentenyl group, a hexenyl group, a heptenyl group, and an octenyl group. As the alkynyl group, examples thereof include alkynyl groups containing preferably from 2 to 15 carbon atoms, more preferably from 2 to 12 carbon atoms, further more preferably from 2 to 8 carbon atoms, which may be straight, branched, or cyclic. Specific examples thereof include an ethynyl group, a propynyl group, a butynyl group, a pentynyl group, a hexynyl group, a heptynyl group, and an octynyl group.

As the aryl group, examples thereof include aryl groups containing preferably from 6 to 30 carbon atoms, more preferably from 6 to 25 carbon atoms, further more preferably from 6 to 20 carbon atoms. Specific examples thereof include a phenyl group, a naphthyl group, an anthryl group, a phenanthrenyl group, a pyrenyl group, and a perylenyl group. As the aralkyl group, examples thereof include those groups which are formed by replacing at least one hydrogen atom of the above-described alkyl group by the above-described aryl group, and specific examples thereof include a benzyl group, a 1-phenylethyl group, a 2-phenylethyl group, a 2-phenyl-2-propyl group, a diphenylmethyl group, a 1,1-diphenylethyl group, and a triphenylmethyl group. As the alkoxy group, examples thereof include alkoxy groups containing preferably from 1 to 15 carbon atoms, more preferably from 1 to 12 carbon atoms, further more preferably from 1 to 8 carbon atoms, which may be straight, branched, or cyclic. Specific examples thereof include a methoxy group, an ethoxy group, a n-propoxy group, an isopropoxy group, a n-butoxy group, a 2-butoxy group, an isobutoxy group, a tert-butoxy group, a n-pentyloxy group, a 2-methylbutoxy group, a 3-methylbutoxy group, a 2,2-dimethylpropyloxy group, a n-hexyloxy group, a 2-methylpentyloxy group, a 3-methylpentyloxy group, a 4-methylpentyloxy group, a 5-methylpentyloxy group, a cyclohexyloxy group, a n-heptyloxy group, and a n-octyloxy group. As the aryloxy group, examples thereof include aryloxy groups containing preferably from 6 to 30 carbon atoms, more preferably from 6 to 25 carbon atoms, further more preferably from 6 to 20 carbon atoms, and specific examples thereof include a phenyloxy group, a naphthyloxy group, and an anthryloxy group.

As the acyl group, examples thereof include acyl groups containing from 1 to 14 carbon atoms which are derived from aliphatic carboxylic acids not having any hydrogen atom at α-position thereof or derived from aromatic carboxylic acid. Specific examples thereof include a trifluoroacetyl group, a pivaloyl group, a benzoyl group, a naphthylcarbonyl group, and an anthrylcarbonyl group.

As the alkylthio group, examples thereof include alkylthio groups containing preferably from 1 to 15, more preferably from 1 to 12, further more preferably from 1 to 8 carbon atoms, which may be straight, branched, or cyclic. Specific examples thereof include a methylthio group, an ethylthio group, a n-propylthio group, an isopropylthio group, a n-butylthio group, a 2-butylthio group, an isobutylthio group, a tert-butylthio group, a n-pentylthio group, a n-hexylthio group, a cyclohexylthio group, a n-heptylthio group, and a n-octylthio group. As the arylthio group, examples thereof include arylthio groups containing preferably from 6 to 30, more preferably from 6 to 25, further more preferably from 6 to 20 carbon atoms, and specific examples thereof include a phenylthio group, a naphthylthio group, and an anthrylthio group.

As the amino group, examples thereof include amino groups wherein two hydrogen atoms on the nitrogen atom are replaced by the above-described hydrocarbyl groups exemplified as the preferable substituent, and specific examples thereof include an N,N-dimethylamino group, an N,N-diethylamino group, an N-methyl-N-phenylamino group, an N,N-diphenylamino group, an N,N-bis(4-methylphenyl) amino group, an N-naphthyl-N-phenylamino group, an N-benzyl-N-phenylamino group, and an N,N-dibenzylamino group. Also, the two hydrocarbyl groups on the nitrogen atom of the amino group may be connected to each other to form a ring. Specific examples thereof include a pyrrolidin-1-yl group, a piperidin-1-yl group, a 1H-pyrrol-1-yl group, a 1H-indol-1-yl group, and a 9H-carbazol-9-yl group. As the silyl group, examples thereof include silyl groups wherein three hydrogen atoms on the silicon atom are replaced by the above-described hydrocarbyl groups exemplified as the preferable substituent, and specific examples thereof include a trimethylsilyl group, a triethylsilyl group, a triisopropylsilyl group, a tert-butyldimethylsilyl group, a dimethylphenylsilyl group, a tert-butyldiphenyl group, and a triphenylsilyl group.

Of these, substituents having an aromatic ring as the partial structure thereof may be substituents wherein the aromatic ring is further substituted by a (pseudo)halogeno group, preferably a chloro group, a bromo group, a (halo)alkanesulfonyloxy group, or an arenesulfonyl group and is capable of reacting with NH-azoles under the conditions in the production process of the invention, that is, the substituents may be active substituents. Specific examples of such active substituents include a chlorophenyl group, a bromophenyl group, a p-toluenesulfonyloxyphenyl group, a (chlorophenyl)methyl group, a (bromophenyl)methyl group, a 2-(chlorophenyl)-2-propyl group, a 2-(bromophenyl)-2-propyl group, a (chlorophenyl) diphenylmethyl group, a (bromophenyl)diphenylmethyl group, a tris(chlorophenyl)methyl group, a tris(bromophenyl)methyl group, a chlorophenyloxy group, a bromophenyloxy group, a chlorophenylthio group, a bromophenylthio group, an N-(chlorophenyl)-N-methylamino group, an N-(bromophenyl)-N-methylamino group, a 5-chloro-1H-indol-1-yl group, a 5-bromo-1H-indol-1-yl group, an N-(chlorophenyl)-N-phenylamino group, an N-(bromophenyl)-N-phenylamino group, an N,N-bis(chlorophenyl)amino group, an N,N-bis(bromophenyl)amino group, a 3,6-dichloro-9H-carbazol-9-yl group, a 3,6-dibromo-9H-carbazol-9-yl group, a (chlorophenyl)dimethylsilyl group, a (bromophenyl)dimethylsilyl group, a (chlorophenyl)diphenylsilyl group, a (bromophenyl)diphenylsilyl group, a tris(chlorophenyl)silyl group, and a tris(bromophenyl)silyl group.

These substituents may further be substituted by an appropriate group selected from the group of the aforementioned substituents. Also, in the case where the (hetero)aryl (pseudo) halides are substituted by a plurality of substituents, the substituents may be connected to each other to form a ring. Further, in the case where the NH-azole is substituted by a plurality of substituents, the substituents may be connected to each other to form a ring.

The basic magnesium compound (hereinafter, referred to as magnesium bases) in the production process of the invention is preferably at least one kind selected from the group consisting of inorganic magnesium bases and organic magnesium bases represented by the following general formula (6):

$$R^{12}-Mg-R^{13} \qquad (6)$$

(wherein Mg represents a magnesium atom, and $R^{12}$ and $R^{13}$ each independently represents a hydrocarbyl group, an alkoxy group, an amino group, or a halogeno group, provided that when $R^{12}$ represents a halogeno group, $R^{13}$ do not represent a halogeno group; and when $R^{13}$ represents a halogeno group, $R^{12}$ do not represent a halogeno group).

Specific examples of the inorganic magnesium bases include magnesium acetate tetrahydrate, basic magnesium tetracarbonate-magnesium hydroxide pentahydrate, magnesium hydride, magnesium hydroxide, magnesium oxide, magnesium phosphate hydrate, and magnesium hydrogenphosphate trihydrate, with magnesium oxide and magnesium hydroxide being preferred in view of reactivity.

In the organic magnesium bases represented by the general formula (6), $R^{12}$ and $R^{13}$ each independently represents a hydrocarbyl group, an alkoxy group, an amino group, or a halogeno group, provided that when $R^{12}$ represents a halogeno group, $R^{13}$ do not represent a halogeno group; and when $R^{13}$ represents a halogeno group, $R^{12}$ do not represent a halogeno group. Examples of the hydrocarbyl group include an alkyl group, an alkenyl group, an aryl group, and an aralkyl group. Of these, examples of the alkyl group includes alkyl groups containing preferably from 1 to 15 carbon atoms, more preferably from 1 to 12 carbon atoms, further more preferably from 1 to 8 carbon atoms, which may be straight, branched, or cyclic. Specific examples thereof include a methyl group, an ethyl group, a n-propyl group, an isopropyl group, a cyclopropyl group, a n-butyl group, an isobutyl group, a sec-butyl group, a tert-butyl group, a n-pentyl group, a cyclopentyl group, a n-hexyl group, a cyclohexyl group, a n-heptyl group, and a n-octyl group. As the alkenyl group, examples thereof include alkenyl groups containing preferably from 2 to 15 carbon atoms, more preferably from 2 to 12 carbon atoms, further more preferably from 2 to 8 carbon atoms, which may be straight, branched, or cyclic. Specific examples thereof include a vinyl group and an allyl group. As the aryl group, examples thereof include aryl groups containing preferably from 6 to 18 carbon atoms, more preferably from 6 to 8 carbon atoms, and specific examples thereof include a phenyl group, a methylphenyl group, and a dimethylphenyl group. As the aralkyl group, examples thereof include aralkyl groups containing preferably from 7 to 19 carbon atoms, more preferably from 7 to 8 carbon atoms, and specific examples thereof include a benzyl group and a methylbenzyl group. As the alkoxy group, examples thereof include alkoxy groups containing preferably from, for example, 1 to 15 carbon atoms, more preferably from 1 to 12 carbon atoms, further more preferably from 1 to 8 carbon atoms, which may be straight, branched, or cyclic. Specific examples thereof include a methoxy group, an ethoxy group, an isopropoxy group, and a tert-butoxy group. As the amino group, examples thereof include amino groups wherein two hydrogen atoms on the nitrogen atom are replaced by the above-described alkyl group or silyl group, and specific examples thereof include a diisopropylamino group, a dicyclohexylamino group, and a bis(trimethylsilyl)amino group. Also, the two alkyl groups on the nitrogen atom of the amino group may be connected to each other to form a ring, and specific examples thereof include a 2,2,6,6-tetramethylpiperidin-1-yl group, and the like. Specific examples of the halogeno group include a chloro group, a bromo group, and an iodo group.

In view of ease of availability, reactivity, and economic efficiency, particularly preferred examples of the organic magnesium bases include those organic magnesium bases wherein $R^{12}$ represents a hydrocarbyl group and $R^{13}$ represents a halogeno group, that is, Grignard reagents. As the Grignard reagents to be used in the production process of the present invention, examples thereof include Grignard reagents containing preferably from 1 to 15 carbon atoms, more preferably from 1 to 12 carbon atoms, further more preferably from 1 to 8 carbon atoms. Specific examples thereof include methylmagnesium chloride, methylmagnesium bromide, methylmagnesium iodide, ethylmagnesium chloride, ethylmagnesium bromide, n-propylmagnesium bromide, isopropylmagnesium chloride, isopropylmagnesium bromide, cyclopropylmagnesium bromide, n-butylmagnesium chloride, isobutylmagnesium bromide, sec-butylmagnesium bromide, tert-butylmagnesium chloride, n-pentylmagnesium bromide, cyclopentylmagnesium bromide, n-hexylmagnesium bromide, cyclohexylmagnesium bromide, n-heptylmagnesium bromide, n-octylmagnesium bromide, vinylmagnesium bromide, allylmagnesium chloride, allylmagnesium bromide, phenylmagnesium chloride, phenylmagnesium bromide, phenylmagnesium iodide, o-tolylmagnesium bromide, m-tolylmagnesium bromide, p-tolylmagnesium bromide, (2,5-dimethylphenyl)magnesium bromide, benzylmagnesium chloride, and benzylmagnesium bromide.

The magnesium bases in the production process of the invention may be used independently or in a proper combination of two or more thereof. The amount of the magnesium salt to be used is not particularly limited, but is properly selected within the range of usually from 0.3 to 10 equivalents, preferably from 0.5 to 5 equivalents, more preferably from 0.8 to 3 equivalents, per mol of the hydrogen atom on the nitrogen atom of the NH-azole.

Additionally, in the production process of the invention, method of adding the magnesium base is not particularly limited, and the magnesium base and the NH-azole may independently be added to the reaction system, the magnesium base and the NH-azole may previously be mixed in a solvent outside the reaction system and added to the reaction system, or they may be added as a magnesium amide synthesized by the reaction between the magnesium base and the NH-azole. Examples of such a magnesium amide include (1H-pyrrol-1-yl)magnesium chloride, methyl(1H-pyrrol-1-yl)magnesium, bis(1H-pyrrol-1-yl)magnesium, (indol-1-yl) magnesium chloride, (indol-1-yl)magnesium chlorideN,N, N',N'-tetramethylethylenediamine complex, (indol-1-yl) magnesium hydroxide, (indol-1-yl)magnesium hexamethyldisilazide, (9H-carbazol-9-yl)magnesium bromide, (9H-carbazol-9-yl)ethylmagnesium, bis(9H-carbazol-9-yl)magnesium.tetrahydrofuran complex, and (9H-carbazol-9-yl)(2,2,6,6-tetramethylpiperidin-1-yl)magnesium.

The production process of the invention is preferably conducted in the presence of a solvent. The solvent is not particularly limited as long as it does not participate in the reaction of the production process of the invention. However, preferred specific examples of the solvent include aliphatic hydrocarbons such as pentane, hexane, heptane, octane, decane, dodecane, undecane, cyclohexane, and decaline; aromatic hydrocarbons such as benzene, toluene, xylene, mesitylene, p-cymene, and diisopropylbenzene; tertiary alcohols such as tert-butanol and 2-methyl-2-butanol; ethers such as diethyl ether, diisopropyl ether, tert-butyl methyl ether, cyclopentyl methyl ether, dimethoxyethane, ethylene glycol diethyl ether, tetrahydrofuran (THF), and 1,4-dioxane; amides such as formamide, N,N-dimethylformamide, and N,N-dimethylacetamide; and water. Specific examples of particularly preferred solvents, in the case where the organic magnesium base is used, include aliphatic hydrocarbons such as pentane, hexane, heptane, octane, decane, dodecane, undecane, cyclohexane, and decaline; aromatic hydrocarbons such as benzene, toluene, xylene, mesitylene, p-cymene, and diisopropylbenzene; and ethers such as diethyl ether, diisopropyl ether, tert-butyl methyl ether, cyclopentyl methyl ether, dimethoxyethane, ethylene glycol diethyl ether, THF, and 1,4-dioxane. These solvents may be used independently or in a proper combination of two or more thereof. The amount of the solvent to be used is not particularly limited as long as the reaction in the production process of the invention sufficiently proceeds, but is properly selected within the range of usually from 0.5 to 200 times by volume, preferably from 1 to 100 times by volume, more preferably from 2 to 50 times by volume based on the weight of the NH-azole.

In the production process of the invention, the reaction temperature is not particularly limited, but is properly selected within the range of from 5 to 300° C., preferably from 10 to 200° C., more preferably from 25 to 150° C. The reaction time naturally varies depending upon kinds of the (hetero)aryl (pseudo)halide and the NH-azole and upon reaction conditions, and is properly selected within the range of from 5 minutes to 72 hours. Also, the production process of the invention is preferably conducted in an inert gas atmosphere. As the inert gas, there are specifically illustrated nitrogen and argon.

The N-(hetero)arylazole obtained by the production process of the invention may be subjected to after-treatment, purification, and isolation, as needed. As the method of after-treatment, examples thereof include, for example, washing of the reaction solution, extraction of the product, filtration of a precipitate, distillation of a solvent, and crystallization by addition of a solvent. These after-treatments may be conducted independently or in combination thereof. As the method of purification and isolation, examples thereof include, for example, decolorization with an adsorbent such as activated carbon or silica gel, column chromatography, distillation, recrystallization, and sublimation. These methods may be conducted independently or in combination thereof.

EXAMPLES

The production process of the invention will be described in detail below by reference to Examples and Comparative Examples which, however, are not to be construed as limiting the invention at all.

Apparatuses and conditions employed in Examples and Comparative Examples for measurement of physical properties are as described below.

Gas chromatography (GC): GC-2010Plus model apparatus (manufactured by Shimadzu Corporation)

Additionally, measuring conditions in GC analysis are as follows.

Column: InertCap 1 (manufactured by GL Sciences); initial temperature: 100° C.; rate of temperature increase: 10° C./min; final temperature: 250° C.; measuring time: 30 minutes.

Nuclear magnetic resonance spectroscopy (NMR): GEMINI2000 model apparatus (manufactured by Varian Medical Systems Inc.)

Additionally, deuterochloroform (CDCl$_3$) was used as a deuterated solvent in NMR analysis, tetramethylsilane (0 ppm) was used as an internal standard substance of $^1$H NMR, CDCl$_3$ itself (77 ppm) was used as an internal standard substance of $^{13}$C NMR, and α,α,α-trifluoro-p-xylene (−64 ppm) was used as an external standard substance of $^{19}$F NMR.

Example 1

Production of N-(4-methylphenyl)carbazole (Structural Formula (8)) (Reaction Formula 2)

Reaction Formula 2

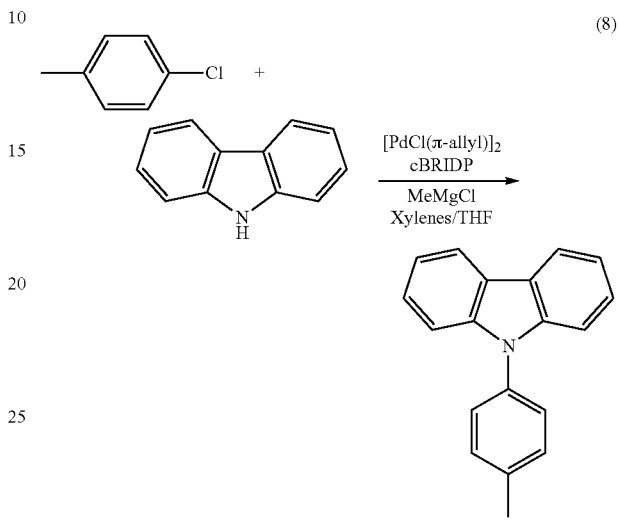

Allylpalladium(II) chloride dimer ([PdCl(π-allyl)]$_2$) (5.8 mg, 0.025 mol %) and di-tert-butyl(2,2-diphenyl-1-methyl-1-cyclopropyl)phosphine (cBRIDP) (22.2 mg, 0.1 mol %) were placed into a 50 mL, two-necked, round bottomed flask equipped a gas inlet, and the flask was evacuated and filled with nitrogen. Subsequently, to the mixture was added dehydrated THF (8.2 mL, 101.0 mmol, 1.6 equivalents), and the mixture was stirred at room temperature for 1 minute to prepare a THF solution of an equivalent mixture of PdCl(π-allyl)(cbridp) and cBRIDP (a catalyst solution) as a pale yellow liquid. Separately, a 200 mL, four-necked, round-bottomed flask equipped with a Teflon® coated magnetic stirring bar, condenser, dropping funnel, thermometer, and a gas inlet was evacuated and filled with nitrogen. Carbazole (10.9 g, 65.0 mmol, 1.03 equivalents) and dehydrated xylenes (66 mL) were charged into the flask, and the mixture was cooled to 5° C. using an ice bath. Subsequently, to the mixture was added a THF solution of methylmagnesium chloride (MeMgCl) (3.22 mol/L, 20.0 mL, 64.4 mmol, 1.02 equivalents) (containing THF in an amount of 17.3 mL (15.4 g, 213.6 mmol, 3.4 equivalents)) dropwise via the dropping funnel over 10 minutes at such a rate that the temperature of the reaction solution was kept at 20° C. or lower, and then the dropping funnel was washed with dehydrated xylenes (11 mL). Subsequently, to the solution were added 4-chlorotoluene (7.5 mL, 63.1 mmol, 1.0 equivalent) and the catalyst solution (8.2 mL) successively, and the solution was stirred for 1 hour under reflux. GC analysis at this point to check progress of the reaction reveals that 4-chlorotoluene (GC retention time: 2.8 minutes) has been completely consumed. After cooling the reaction mixture to room temperature, to the mixture were added water (25 mL) and ammonium chloride (1.7 g, 31.8 mmol, 0.5 equivalents). The aqueous layer was separated off, and the organic layer was concentrated under reduced pressure to give oily residue, which was purified by silica gel column chromatography (eluent: n-hexane/toluene=2/1) to afford 16.0 g of N-(4-methylphenyl)carbazole as a white powder.

Isolated yield: 98.5%.

$^1$H NMR (300 MHz, CDCl$_3$): 2.48 (s, 3H), 7.23-7.30 (m, 2H), 7.35-7.45 (m, 8H), 8.14 (dt, J=7.5, 0.9 Hz, 2H).

$^{13}$C NMR (75 MHz, CDCl$_3$): 21.2, 109.8, 119.7, 120.2, 123.2, 125.8, 127.0, 130.4, 135.0, 137.3, 141.1.

Example 2

Production of N-(4-methylphenyl)carbazole (Structural Formula (8)) Using di-tert-butyl(2,2-diphenyl-1-methylvinyl)phosphine (vBRIDP) as a Coordination Compound The reaction was conducted for 3 hours in the same experimental procedures as in Example 1 except for using vBRIDP (21.4 mg, 0.1 mol %) as a coordination compound, and 15.9 g of N-(4-methylphenyl)carbazole was obtained as a white powder.

Isolated yield: 98.0%.

Example 3

Production of N-(4-methylphenyl)carbazole (Structural Formula (8)) Using 2-di-tert-butylphosphino-2',4',6'-triisopropylbiphenyl (tBuXPhos) as a Coordination Compound The reaction was conducted for 3 hours in the same experimental procedures as in Example 1 except for using tBuXPhos (26.8 mg, 0.1 mol %) as a coordination compound, and then, 14.3 g of N-(4-methylphenyl)carbazole was obtained as a white powder.

Isolated yield: 88.1%.

The results of Examples 1 to 3 are summarized in Table 1.

TABLE 1

| Ex. | Coordination Compound | Reaction Time | Isolated Yield |
|---|---|---|---|
| 1 | cBRIDP | 1 hr | 98.5% |
| 2 | vBRIDP | 3 hrs | 98.0% |
| 3 | tBuXPhos | 3 hrs | 88.1% |

It has become apparent from these results that, in the production process of the invention, various electron-rich, bulky coordination compounds can preferably be used.

Example 4

Production of N-(4-methoxyphenyl)carbazole (Structural Formula (9))

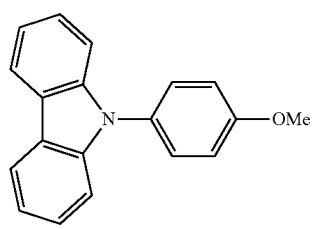

(9)

[PdCl(π-allyl)]$_2$ (23.1 mg, 0.1 mol %) and cBRIDP (89.0 mg, 0.4 mol %) were placed into a 50 mL, two-necked, round bottomed flask equipped a gas inlet, and the flask was evacuated and filled with nitrogen. Subsequently, to the mixture was added dehydrated THF (8.2 mL, 101.0 mmol, 1.6 equivalents) to prepare a catalyst solution. A 200 mL, four-necked, round-bottomed flask equipped with a Teflon® coated magnetic stirring bar, condenser, dropping funnel, thermometer, and a gas inlet was evacuated and filled with nitrogen. Carbazole (10.9 g, 65.0 mmol, 1.03 equivalents) and dehydrated xylenes (66 mL) were charged into the flask, and the mixture was cooled to 5° C. using an ice bath. Subsequently, to the mixture was added a THF solution of MeMgCl (3.22 mol/L, 20.0 mL, 64.4 mmol, 1.02 equivalents) dropwise via the dropping funnel at such a rate that the temperature of the reaction solution was kept at 20° C. or lower, and then the dropping funnel was washed with dehydrated xylenes (11 mL). Subsequently, to the solution were added 4-chloroanisole (7.7 mL, 63.1 mmol, 1.0 equivalent) and the catalyst solution (8.2 mL) successively, and the solution was stirred for 1 hour under reflux. After cooling the reaction mixture to room temperature, to the mixture were added water (25 mL) and ammonium chloride (1.7 g). The aqueous layer was separated off, and the organic layer was concentrated under reduced pressure to give solid residue. The residue was dissolved in toluene, and the solution was decolorized by silica gel (1 g) and filtered through a Celite pad. The filtrate was concentrated under reduced pressure to give the solid, which was recrystallized from toluene/methanol to afford 16.1 g of N-(4-methoxylphenyl)carbazole as a white powder.

Isolated yield: 93.3%.

$^1$H NMR (300 MHz, CDCl$_3$): 3.91 (s, 3H), 7.08-7.14 (m, 2H), 7.27 (ddd, J=1.2, 6.9, 7.8 Hz, 2H), 7.32 (d, J=8.1 Hz, 2H), 7.40 (ddd, J=1.2, 6.9, 8.1 Hz, 2H), 7.42-7.48 (m, 2H), 8.14 (d, J=7.5 Hz, 2H).

$^{13}$C NMR (75 MHz, CDCl$_3$): 55.6, 109.7, 115.1, 119.6, 120.2, 123.1, 125.8, 128.6, 130.3, 141.4, 158.9.

Example 5

Production of N-(3-methylphenyl)carbazole (Structural Formula (10))

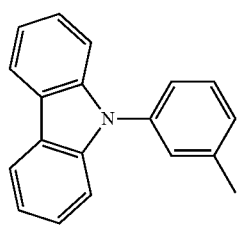

(10)

The reaction was conducted for 1 hour in the same experimental procedures as in Example 1 except for using 3-chlorotoluene (7.4 mL, 63.1 mmol, 1.0 equivalent) as an aryl halide, and 16.1 g of N-(3-methylphenyl)carbazole was obtained as a colorless viscous liquid.

Isolated yield: 99.1%.

$^1$H NMR (300 MHz, CDCl$_3$): 2.46 (s, 3H), 7.24-7.31 (m, 9H), 7.48 (dt, J=0.9, 7.5 Hz, 1H), 8.14 (dt, J=7.8, 0.9 Hz, 2H).

$^{13}$C NMR (75 MHz, CDCl$_3$): 21.4, 109.8, 119.8, 120.2, 123.3, 124.1, 125.8, 127.7, 128.2, 129.6, 137.6, 139.9, 140.9.

Example 6

Production of N-Phenylcarbazole (Structural Formula (11))

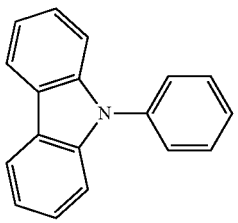

(11)

The reaction was conducted for 30 minutes in the same experimental procedures as in Example 1 except for using chlorobenzene (6.4 mL, 63.1 mmol, 1.0 equivalent) as an aryl halide, and 15.2 g of N-phenylcarbazole was obtained as a white powder.

Isolated yield: 99.0%.

$^1$H NMR (300 MHz, CDCl$_3$): 7.25-7.33 (m, 2H), 7.38-7.50 (m, 5H), 7.53-7.64 (m, 4H), 8.16 (dt, J=7.8, 0.9 Hz, 2H).

$^{13}$C NMR (75 MHz, CDCl$_3$): 109.7, 119.9, 120.3, 123.3, 125.9, 127.1, 127.4, 129.8, 137.7, 140.9.

Example 7

Production of N-Phenylcarbazole (Structural Formula (11)) by Using Bromobenzene as an Aryl Halide The reaction was conducted for 1 hour in the same experimental procedures as in Example 1 except for using bromobenzene (6.6 mL, 63.1 mmol, 1.0 equivalent) as an aryl halide, and 15.0 g of N-phenylcarbazole was obtained as a white powder.

Isolated yield: 97.7%.

Example 8

Production of N-(4-chlorophenyl)carbazole (Structural Formula (12))

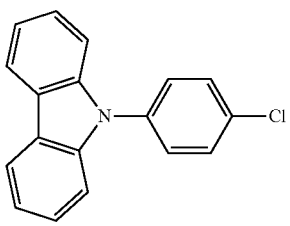

(12)

The reaction was conducted for 2 hours in the same experimental procedures as in Example 1 except for using 4-bromochlorobenzene (12.1 g, 63.1 mmol, 1.0 equivalent) as an aryl halide, and 17.5 g of N-(4-chlorophenyl)carbazole, was obtained as a white powder. Purity: 96.8 wt % (due to contamination of 2.0 mol % of 1,4-bis(N-carbazolyl)benzene as a by-product).

Isolated yield: 96.7%.

$^1$H NMR (300 MHz, CDCl$_3$): 7.29 (ddd, J=1.5, 6.6, 8.1 Hz, 2H), 7.36 (d, J=7.8 Hz, 2H), 7.41 (ddd, J=1.2, 6.6, 8.1 Hz, 2H), 7.50 (dt, J=8.7, 2.4 Hz, 2H), 7.57 (dt, J=9.0, 2.4 Hz, 2H), 8.14 (dt, J=7.8, 0.9 Hz, 2H).

$^{13}$C NMR (75 MHz, CDCl$_3$): 109.8, 120.4, 120.6, 123.7, 126.3, 128.7, 130.4, 133.3, 136.5, 140.9.

Example 9

Production of N-(4-trifluoromethylphenyl)carbazole (Structural Formula (13))

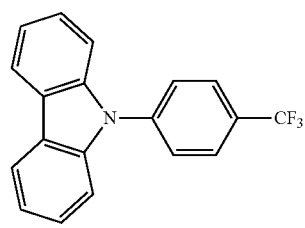

(13)

The reaction was conducted for 15 minutes in the same experimental procedures as in Example 1 except for using 4-chlorobenzotrifluoride (8.4 mL, 63.1 mmol, 1.0 equivalent) as an aryl halide. After cooling the reaction mixture to room temperature, to the mixture were added water (25 mL) and ammonium chloride (1.7 g). The aqueous layer was separated off, and the organic layer was concentrated under reduced pressure to give solid residue. The residue was dissolved in toluene, and the solution was decolorized by silica gel (1 g) and filtered through a Celite pad. The filtrate was concentrated under reduced pressure to give the solid, which was recrystallized from toluene/methanol to afford 18.4 g of N-(4-trifluoromethylphenyl)carbazole as a white powder.

Isolated yield: 93.7%.

$^1$H NMR (300 MHz, CDCl$_3$): 7.28-7.35 (m, 2H), 7.38-7.46 (m, 4H), 7.72 (d, J=8.7 Hz, 2H), 7.88 (d, J=8.4 Hz, 2H), 8.15 (dd, J=1.2, 7.8 Hz, 2H).

$^{13}$C NMR (75 MHz, CDCl$_3$): 109.6, 120.5, 120.6, 123.7, 126.2, 127.05, 127.12, 140.3, 141.1.

$^{19}$F NMR (282 MHz, CDCl$_3$): −63.9.

Example 10

Production of N-(4-benzoylphenyl)carbazole (Structural Formula (14))

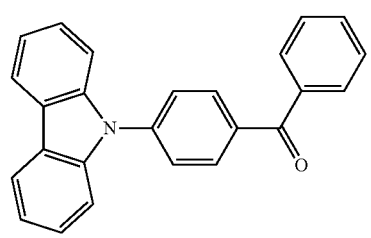

(14)

The reaction was conducted for 15 minutes in the same experimental procedures as in Example 1 except for using 4-chlorobenzophenone (14.1 g, 63.1 mmol, 1.0 equivalent) as an aryl halide, and 22.2 g of N-(4-benzoylphenyl)carbazole was obtained as a pale yellow solid.

Isolated yield: 99.2%.

$^1$H NMR (300 MHz, CDCl$_3$): 7.32 (ddd, J=0.9, 7.2, 8.1 Hz, 2H), 7.44 (ddd, J=1.2, 7.2, 8.1 Hz, 2H), 7.49-7.59 (m, 4H), 7.60-7.68 (m, 1H), 7.70-7.76 (m, 2H), 7.87-7.94 (m, 2H), 8.04-8.11 (m, 2H), 8.15 (d, J=7.8 Hz, 2H).

$^{13}$C NMR (75 MHz, CDCl$_3$): 109.8, 120.4, 120.6, 123.8, 126.2, 126.3, 128.4, 130.0, 131.9, 132.6, 136.0, 137.5, 140.3, 141.7, 195.6.

Example 11

Production of N-(4-cyanophenyl)carbazole (Structural Formula (15))

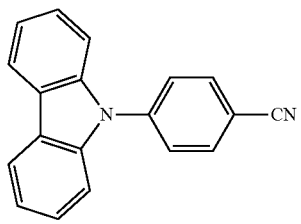

(15)

The reaction was conducted for 30 minutes in the same experimental procedures as in Example 9 except for using 4-chlorobenzonitrile (8.7 g, 63.1 mmol, 1.0 equivalent) as an aryl halide, and 16.0 g of N-(4-cyanophenyl)carbazole was obtained as a white powder.

Isolated yield: 92.6%.

$^1$H NMR (300 MHz, CDCl$_3$): 7.33 (ddd, J=2.7, 5.7, 8.1 Hz, 2H), 7.40-7.48 (m, 4H), 7.74 (dt, J=8.7, 2.1 Hz, 2H), 7.87-7.94 (m, 2H), 8.14 (d, J=7.8 Hz, 2H).

$^{13}$C NMR (75 MHz, CDCl$_3$): 109.5, 110.5, 118.3, 120.6, 121.0, 124.0, 126.4, 127.1, 133.9, 139.9, 142.1.

Example 12

Production of 2-(N-carbazolyl)thiophene (Structural Formula (16))

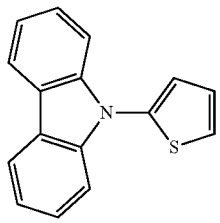

(16)

[PdCl(π-allyl)]$_2$ (23.1 mg, 0.1 mol %) and cBRIDP (89.0 mg, 0.4 mol %) were placed into a 50 mL, two-necked, round bottomed flask equipped a gas inlet, and the flask was evacuated and filled with nitrogen. Subsequently, to the mixture was added dehydrated THF (8.2 mL, 101.0 mmol, 1.6 equivalents) to prepare a catalyst solution. A 200 mL, four-necked, round-bottomed flask equipped with a Teflon® coated magnetic stirring bar, condenser, dropping funnel, thermometer, and a gas inlet was evacuated and filled with nitrogen. Carbazole (10.9 g, 65.0 mmol, 1.03 equivalents) and dehydrated xylenes (66 mL) were charged into the flask, and the mixture was cooled to 5° C. using an ice bath. Subsequently, to the mixture was added a THF solution of MeMgCl (3.22 mol/L, 20.0 mL, 64.4 mmol, 1.02 equivalents) dropwise via the dropping funnel at such a rate that the temperature of the reaction solution was kept at 20° C. or lower, and then the dropping funnel was washed with dehydrated xylenes (11 mL). Subsequently, to the solution were added 2-chlorothiophene (5.8 mL, 63.1 mmol, 1.0 equivalent) and the catalyst solution (8.2 mL) successively, and the solution was stirred for 2 hours under reflux. After cooling the reaction mixture to room temperature, to the mixture were added water (25 mL) and ammonium chloride (1.7 g). The aqueous layer was separated off, and the organic layer was concentrated under reduced pressure to give oily residue, which was purified by silica gel chromatography (eluent: n-hexane/toluene=2/1) to afford 15.4 g of 2-(N-carbazolyl)thiophene as a pale yellow solid.

Isolated yield: 97.9%.

$^1$H NMR (300 MHz, CDCl$_3$): 7.15-7.23 (m, 2H), 7.30 (ddd, J=2.4, 6.0, 8.1 Hz, 2H), 7.38 (dd, J=1.8, 5.4 Hz, 1H), 7.39-7.48 (m, 4H), 8.10 (d, J=7.5 Hz, 2H).

$^{13}$C NMR (75 MHz, CDCl$_3$): 110.2, 120.2, 120.5, 123.5, 124.2, 124.8, 126.19, 126.22, 142.0.

Example 13

Production of 2-(N-carbazolyl)pyridine (Structural Formula (17))

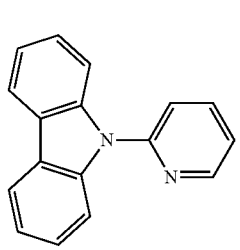

(17)

The reaction was conducted for 1 hour in the same experimental procedures as in Example 12 except for using 2-chloropyridine (6.0 mL, 63.1 mmol, 1.0 equivalent) as a heteroaryl halide, and purification was conducted by using toluene/triethylamine=100/1 as an eluent for silica gel column chromatography, and 15.1 g of 2-(N-carbazolyl)pyridine was obtained as a white powder.

Isolated yield: 98.0%.

$^1$H NMR (300 MHz, CDCl$_3$): 7.29 (dd, J=0.9, 7.5 Hz, 1H), 7.31 (dt, J=0.9, 7.5 Hz, 2H), 7.44 (ddd, J=1.2, 7.2, 8.4 Hz, 2H), 7.64 (dt, J=0.9, 8.4 Hz, 1H), 7.84 (d, J=8.1 Hz, 2H), 7.92 (ddd, J=2.1, 7.5, 8.1 Hz, 1H), 8.12 (ddd, J=0.9, 1.5, 7.8 Hz, 2H), 8.73 (ddd, J=0.9, 1.8, 4.8 Hz, 1H).

$^{13}$C NMR (75 MHz, CDCl$_3$): 111.1, 119.1, 120.2, 120.9, 121.2, 124.3, 126.2, 138.4, 139.6, 149.6, 151.9.

Example 14

Production of 2-(N-carbazolyl)quinoline (Structural Formula (18))

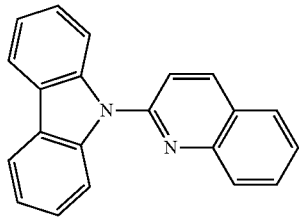

(18)

The reaction was conducted for 15 minutes in the same experimental procedures as in Example 12 except for using 2-chloroquinoline (10.3 g, 63.1 mmol, 1.0 equivalent) as a heteroaryl halide, and purification was conducted by using toluene/triethylamine=100/1 as an eluent for silica gel column chromatography, and 18.3 g of 2-(N-carbazolyl)quinoline was obtained as a pale yellow solid.

Isolated yield: 98.5%.

$^1$H NMR (300 MHz, CDCl$_3$): 7.34 (ddd, J=1.2, 7.8, 8.4 Hz, 2H), 7.47 (ddd, J=1.2, 7.2, 8.4 Hz, 2H), 7.59 (ddd, J=0.9, 6.9, 8.1 Hz, 1H), 7.75-7.84 (m, 2H), 7.91 (dd, J=1.2, 8.4 Hz, 1H), 8.01 (dt, J=8.4, 0.9 Hz, 2H), 8.10-8.20 (m, 3H), 8.35 (d, J=9.0 Hz, 1H).

$^{13}$C NMR (75 MHz, CDCl$_3$): 111.6, 117.7, 120.2, 121.2, 124.6, 126.30, 126.34, 126.5, 127.6, 128.8, 130.3, 138.7, 139.6, 147.7, 150.9.

Example 15

Production of N-(2-naphthyl)carbazole (Structural Formula (19)) Using 2-(p-toluenesulfonyloxy)naphthalene (2-naphthyl tosylate) as an Aryl Pseudohalide (Reaction Formula 3)

Reaction Formula 3

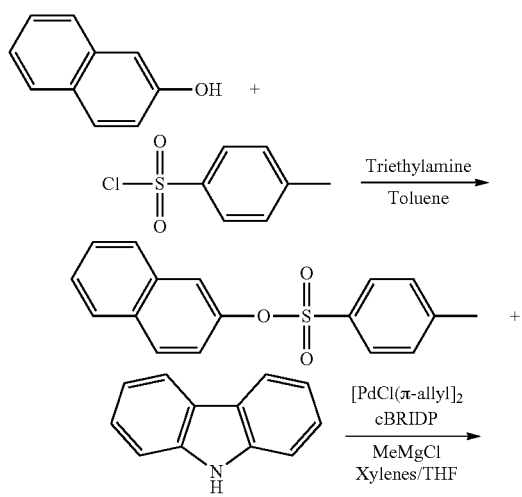

(19)

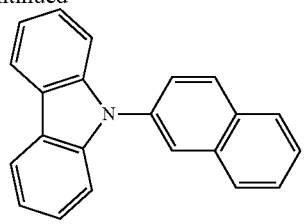

N-(2-naphthyl)carbazole was prepared by using an aryl pseudohalide prepared from 2-naphthol which is available inexpensively, in place of hardly available 2-halonaphthalenes (2-chloronaphthalene is not commercially available, and 2-bromonaphthalene is expensive and containing small amount (up to 3%) of 1-bromonaphthalene as an impurity).

A 2 L four-necked round-bottomed flask equipped with a Teflon® coated magnetic stirring bar, dropping funnel, thermometer, and a gas inlet was evacuated and filled with nitrogen. 2-naphthol (51.8 g, 359.3 mmol, 1.0 equivalent), dehydrated toluene (800 mL), and triethylamine (52.6 mL, 377.3 mmol, 1.05 equivalents) were charged into the flask successively. Subsequently, to the solution was added p-toluenesulfonyl chloride (69.9 g, 366.5 mmol, 1.02 equivalents) in dehydrated toluene (140 mL) dropwise via the dropping funnel over 15 minutes at such a rate that the internal temperature was kept at 50° C. or lower, and the mixture was stirred for further 2 hours at room temperature. The thus-obtained white suspension was poured into water, and the aqueous layer was separated off. The organic layer was passed through a silica gel pad, and concentrated under reduced pressure to give solid residue, which was purified by recrystallization from toluene/methanol to afford 94.2 g of 2-naphthyl tosylate as a white powder. The mother liquor was concentrated under reduced pressure to give solid residue, which was recrystallized to recover further 9.2 g of 2-naphthyl tosylate.

Isolated yield: 96.5%.

$^1$H NMR (300 MHz, CDCl$_3$): 2.44 (s, 3H), 7.10 (dd, J=2.4, 9.0 Hz, 1H), 7.29 (d, J=7.8 Hz, 2H), 7.45-7.52 (m, 3H), 7.70-7.84 (m, 5H).

[PdCl(π-allyl)]$_2$ (5.8 mg, 0.05 mol %) and cBRIDP (22.2 mg, 0.2 mol %) were placed into a 50 mL, two-necked, round bottomed flask equipped a gas inlet, and the flask was evacuated and filled with nitrogen. Subsequently, to the mixture was added dehydrated THF (4.1 mL, 50.5 mmol, 1.6 equivalents) to prepare a catalyst solution. A 200 mL, four-necked, round-bottomed flask equipped with a Teflon® coated magnetic stirring bar, condenser, dropping funnel, thermometer, and a gas inlet was evacuated and filled with nitrogen. Carbazole (5.4 g, 32.5 mmol, 1.03 equivalents) and dehydrated xylenes (33 mL) were charged into the flask, and the mixture was cooled to 5° C. using an ice bath. Subsequently, to the mixture was added a THF solution of MeMgCl (3.22 mol/L, 10.0 mL, 32.2 mmol, 1.02 equivalents) dropwise via the dropping funnel at such a rate that the temperature of the reaction solution was kept at 20° C. or lower, and then the dropping funnel was washed with dehydrated xylenes (6 mL). Subsequently, to the solution were added 2-naphthyl tosylate (9.4 g, 31.6 mmol, 1.0 equivalent) and the catalyst solution (4.1 mL) successively, and the solution was stirred for 15 minutes under reflux. After cooling the reaction mixture to room temperature, to the mixture were added water (100 mL) and ammonium chloride (850 mg). The aqueous layer was separated off, and the organic layer was concentrated under reduced pressure to give solid residue. The residue was dissolved in toluene, and the solution was decolorized by silica gel (500 mg) and filtered through a Celite pad. The filtrate was concentrated under reduced pressure to give the solid, which was recrystallized from toluene/methanol to afford 8.5 g of N-(2-naphthyl)carbazole as a white powder.

Isolated yield: 91.6%.

$^1$H NMR (300 MHz, CDCl$_3$): 7.30 (ddd, J=1.5, 6.6, 7.8 Hz, 2H), 7.41 (ddd, J=1.2, 6.6, 8.1 Hz, 2H), 7.47 (ddd, J=0.9, 1.5, 8.1 Hz, 2H), 7.54-7.61 (m, 2H), 7.66 (dd, J=2.1, 8.7 Hz, 1H), 7.86-8.00 (m, 2H), 8.05-8.09 (m, 2H), 8.17 (dt, J=7.5, 0.9 Hz, 2H).

$^{13}$C NMR (75 MHz, CDCl$_3$): 109.8, 120.0, 120.3, 123.4, 125.3, 125.4, 126.0, 126.5, 126.8, 127.86, 127.93, 129.8, 132.4, 134.0, 135.2, 141.1.

The results of Examples 4 to 15 are summarized in Table 2.

TABLE 2

| Ex. | (Hetero)aryl (Pseudo)halide | Amount of Palladium Catalyst | Reaction Time | Isolated Yield | Purification Method |
|---|---|---|---|---|---|
| 4 | 4-Chloroanisole | 0.2 mol % | 1 hr | 93.3% | Recrystallization |
| 5 | 3-Chlorotoluene | 0.05 mol % | 1 hr | 99.1% | Column |
| 6 | Chlorobenzene | 0.05 mol % | 30 min | 99.0% | Column |
| 7 | Bromobenzene | 0.05 mol % | 1 hr | 97.7% | Column |
| 8 | 4-Bromochlorobenzene | 0.05 mol % | 2 hrs | 96.7% | Column |
| 9 | 4-Chlorobenzotrifluoride | 0.05 mol % | 15 min | 93.7% | Recrystallization |
| 10 | 4-Chlorobenzophenone | 0.05 mol % | 15 min | 99.2% | Column |
| 11 | 4-Chlorobenzonitrile | 0.05 mol % | 30 min | 92.6% | Recrystallization |
| 12 | 2-Chlorothiophene | 0.2 mol % | 2 hrs | 97.9% | Column |
| 13 | 2-Chloropyridine | 0.2 mol % | 1 hr | 98.0% | Column |
| 14 | 2-Chloroquinoline | 0.2 mol % | 15 min | 98.5% | Column |
| 15 | 2-Naphthyl Tosylate | 0.1 mol % | 15 min | 91.6% | Recrystallization |

It has become apparent from these results that, in the production process of the invention, various (hetero)aryl (pseudo)halides can preferably be used.

Example 16

Production of 1,3-bis(N-carbazolyl)benzene (mCP, Structural Formula (20))

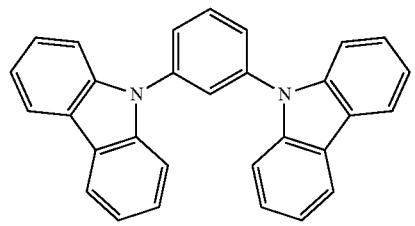

(20)

[PdCl(π-allyl)]$_2$ (11.6 mg, 0.1 mol %) and cBRIDP (44.4 mg, 0.4 mol %) were placed into a 50 mL, two-necked, round bottomed flask equipped a gas inlet, and the flask was evacuated and filled with nitrogen. Subsequently, to the mixture was added dehydrated THF (8.2 mL, 101.0 mmol, 3.2 equivalents) to prepare a catalyst solution. A 200 mL, four-necked, round-bottomed flask equipped with a Teflon® coated magnetic stirring bar, condenser, dropping funnel, thermometer, and a gas inlet was evacuated and filled with nitrogen. Carbazole (10.9 g, 65.0 mmol, 2.06 equivalents) and dehydrated xylenes (66 mL) were charged into the flask, and the mixture was cooled to 5° C. using an ice bath. Subsequently, to the mixture was added a THF solution of MeMgCl (3.22 mol/L, 20.0 mL, 64.4 mmol, 2.04 equivalents) dropwise via the dropping funnel at such a rate that the temperature of the reaction solution was kept at 20° C. or lower, and then the dropping funnel was washed with dehydrated xylenes (11 mL). Subsequently, to the solution were added 1,3-dichlorobenzene (3.6 mL, 31.6 mmol, 1.0 equivalent) and the catalyst solution (8.2 mL) successively, and the solution was stirred for 10 minutes under reflux. After cooling the reaction mixture to room temperature, to the mixture were added water (25 mL) and ammonium chloride (1.7 g). The aqueous layer was separated off, and the organic layer was concentrated under reduced pressure to give solid residue. The residue was dissolved in toluene, and the solution was decolorized by silica gel (1 g) and filtered through a Celite pad. The filtrate was concentrated under reduced pressure to give the solid, which was recrystallized from toluene/methanol to afford 12.5 g of mCP as a white powder.

Isolated yield: 96.8%.

$^1$H NMR (300 MHz, CDCl$_3$): 7.31 (ddd, J=1.2, 6.6, 7.8 Hz, 4H), 7.44 (ddd, J=1.2, 6.9, 8.1 Hz, 4H), 7.54 (d, J=8.1 Hz, 4H), 7.70 (dd, J=2.1, 7.5 Hz, 2H), 7.80-7.88 (m, 2H), 8.15 (d, J=7.8 Hz, 4H).

$^{13}$C NMR (75 MHz, CDCl$_3$): 109.7, 120.3, 120.4, 123.6, 125.3, 125.8, 126.1, 131.2, 139.4, 140.6.

Example 17

Production of 1,4-bis(N-carbazolyl)benzene (pCP, Structural Formula (21))

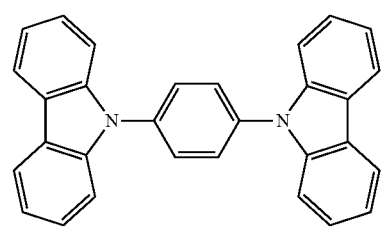

(21)

The reaction was conducted for 10 minutes in the same experimental procedures as in Example 16 except for using 1,4-dichlorobenzene (4.6 g, 31.6 mmol, 1.0 equivalent) as an aryl halide. To the reaction mixture was added an aqueous solution of ammonium chloride, and the mixture was poured into chloroform (800 mL). The aqueous layer was separated off, and the organic layer was passed through a silica gel pad and concentrated to remove the excess chloroform under reduced pressure. To the thus-obtained suspension was added methanol (130 mL), and the crystal was collected from the suspension by suction filtration, washed with methanol and dried under reduced pressure to afford 12.6 g of pCP as a white powder.

Isolated yield: 97.6%.

$^1$H NMR (300 MHz, CDCl$_3$): 7.34 (ddd, J=0.9, 6.9, 7.8 Hz, 4H), 7.48 (ddd, J=1.2, 6.9, 8.1 Hz, 4H), 7.57 (d, J=8.4 Hz, 4H), 7.83 (s, 4H), 8.19 (d, J=7.8 Hz, 4H).

$^{13}$C NMR (75 MHz, CDCl$_3$): 109.7, 120.3, 120.4, 123.6, 126.1, 128.4, 136.7, 140.8.

Example 18

Production of 4,4'-bis(N-carbazolyl)biphenyl (CBP, Structural Formula (22))

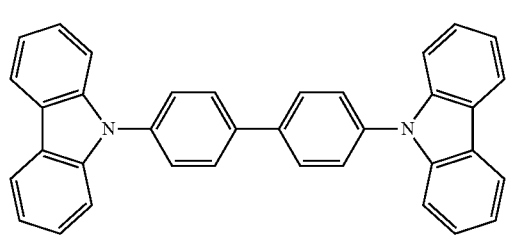

(22)

The reaction was conducted for 15 minutes in the same experimental procedures as in Example 16 except for using 4,4'-dibromobiphenyl (9.8 g, 31.6 mol, 1.0 equivalent) as an aryl halide. To the reaction mixture was added an aqueous solution of ammonium chloride, and the mixture was poured into chloroform (500 mL). The aqueous layer was separated off, and the organic layer was passed through a silica gel pad and concentrated to remove the excess chloroform under reduced pressure. To the thus-obtained suspension was added methanol (150 mL), and the crystal was collected from the suspension by suction filtration, washed with methanol and dried under reduced pressure to afford 14.9 g of CBP as a pale yellow powder.

Isolated yield: 97.3%.

$^1$H NMR (300 MHz, CDCl$_3$): 7.32 (ddd, J=1.2, 6.9, 7.8 Hz, 4H), 7.45 (ddd, J=1.2, 6.9, 8.1 Hz, 4H), 7.52 (d, J=7.8 Hz, 414), 7.68-7.74 (m, 4H), 7.88-7.95 (m, 4H), 8.18 (d, J=7.5 Hz, 4H).

$^{13}$C NMR (75 MHz, CDCl$_3$): 110.6, 120.3, 120.6, 123.7, 126.2, 127.7, 128.8, 137.5, 139.5, 141.1.

Example 19

Production of 2,6-bis(N-carbazoyl)pyridine (26mCPy, Structural Formula (23))

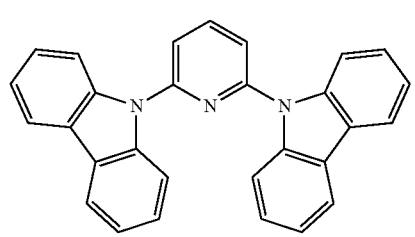

(23)

[PdCl(π-allyl)]$_2$ (23.1 mg, 0.2 mol %) and cBRIDP (89.0 mg, 0.8 mol %) were placed into a 50 mL, two-necked, round bottomed flask equipped a gas inlet, and the flask was evacuated and filled with nitrogen. Subsequently, to the mixture was added dehydrated THF (8.2 mL, 101.0 mmol, 3.2 equivalents) to prepare a catalyst solution. A 200 mL, four-necked, round-bottomed flask equipped with a Teflon® coated magnetic stirring bar, condenser, dropping funnel, thermometer, and a gas inlet was evacuated and filled with nitrogen. Carbazole (10.9 g, 65.0 mmol, 2.06 equivalents) and dehydrated xylenes (66 mL) were charged into the flask, and the mixture was cooled to 5° C. using an ice bath. Subsequently, to the mixture was added a THF solution of MeMgCl (3.22 mol/L, 20.0 mL, 64.4 mmol, 2.04 equivalents) dropwise via the dropping funnel at such a rate that the temperature of the reaction solution was kept at 20° C. or lower, and then the dropping funnel was washed with dehydrated xylenes (11 mL). Subsequently, to the solution were added 2,6-dichloropyridine (4.7 g, 31.6 mmol, 1.0 equivalent) and the catalyst solution (8.2 mL) successively, and the solution was stirred for 15 minutes under reflux. After cooling the reaction mixture to 50° C., to the mixture were added toluene (70 mL), water (25 mL) and ammonium chloride (1.7 g). The aqueous layer was separated off at 50° C., and the organic layer was concentrated to remove remaining THF and water under reduced pressure and decolorized by silica gel (1 g) and filtered through a Celite pad. The filtrate was concentrated under reduced pressure to give the solid, which was recrystallized from toluene/methanol to afford 11.8 g of 26mCPy as a white powder.

Isolated yield: 91.2%.

$^1$H NMR (300 MHz, CDCl$_3$): 7.33 (dt, J=0.9, 7.5 Hz, 4H), 7.41 (dt, J=1.2, 7.2 Hz, 4H), 7.63 (d, J=8.1 Hz, 2H), 8.02 (d, J=8.1 Hz, 2H), 8.08-8.15 (m, 5H).

$^{13}$C NMR (75 MHz, CDCl$_3$): 111.9, 114.9, 120.1, 121.2, 124.6, 126.3, 139.5, 140.4, 151.6.

Example 20

Production of 1,3,5-tris(N-carbazolyl)benzene (tCP, Structural Formula (24))

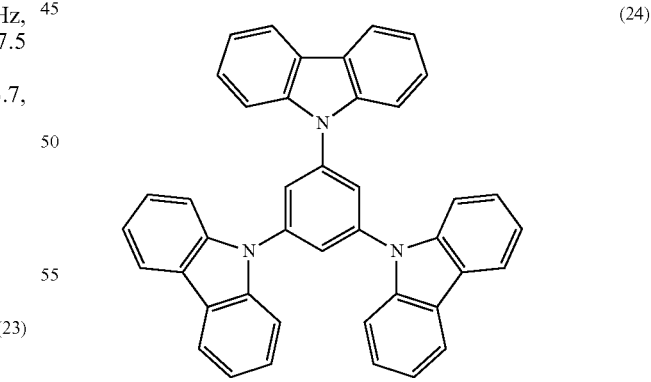

(24)

[PdCl(π-allyl)]$_2$ (11.6 mg, 0.15 mol %) and cBRIDP (44.4 mg, 0.6 mol %) were placed into a 50 mL, two-necked, round bottomed flask equipped a gas inlet, and the flask was evacuated and filled with nitrogen. Subsequently, to the mixture was added dehydrated THF (8.2 mL, 101.0 mmol, 4.8 equivalents) to prepare a catalyst solution. A 200 mL, four-necked, round-bottomed flask equipped with a Teflon® coated magnetic stirring bar, condenser, dropping funnel, thermometer, and a gas inlet was evacuated and filled with nitrogen. Carbazole (10.9 g, 65.0 mmol, 3.09 equivalents) and dehydrated xylenes (66 mL) were charged into the flask, and the mixture was cooled to 5° C. using an ice bath. Subsequently, to the mixture was added a THF solution of MeMgCl (3.22 mol/L, 20.0 mL, 64.4 mmol, 3.06 equivalents) dropwise via the dropping funnel at such a rate that the temperature of the reaction solution was kept at 20° C. or lower, and then the dropping funnel was washed with dehydrated xylenes (11 mL). Subsequently, to the solution were added 1,3,5-trichlorobenzene (3.8 g, 21.0 mmol, 1.0 equivalent) and the catalyst solution (8.2 mL) successively, and the solution was stirred for 10 minutes under reflux. To the reaction mixture was added an aqueous solution of ammonium chloride, and the mixture was poured into chloroform (1,200 mL). The aqueous layer was separated off, and the organic layer was passed through a silica gel pad and concentrated to remove the excess chloroform under reduced pressure. To the thus-obtained suspension was added methanol (200 mL), and the crystal was collected from the suspension by suction filtration, washed with methanol and dried under reduced pressure to afford 11.4 g of tCP as a white powder.

Isolated yield: 94.6%.

$^1$H NMR (300 MHz, CDCl$_3$): 7.34 (ddd, J=0.9, 6.9, 7.8 Hz, 6H), 7.48 (ddd, J=1.2, 7.2, 8.4 Hz, 6H), 7.67 (d, J=8.1 Hz, 6H), 7.96 (s, 3H), 8.17 (d, J=7.8 Hz, 6H).

$^{13}$C NMR (75 MHz, CDCl$_3$): 109.7, 120.6, 120.7, 123.5, 123.9, 126.4, 140.3, 140.8.

The results of Examples 16 to 20 are summarized in Table 3.

TABLE 3

| Ex. | (Hetero)aryl Halide | Amount of Palladium Catalyst | Reaction Time | Isolated Yield | Purification Method | Product |
|---|---|---|---|---|---|---|
| 16 | 1,3-Dichlorobenzene | 0.2 mol % | 10 min | 96.8% | Recrystallization | mCP |
| 17 | 1,4-Dichlorobenzene | 0.2 mol % | 10 min | 97.6% | Crystallization | pCP |
| 18 | 4,4'-Dibromobiphenyl | 0.2 mol % | 15 min | 97.3% | Crystallization | CBP |
| 19 | 2,6-Dichloropyridine | 0.4 mol % | 15 min | 91.2% | Recrystallization | 26mCPy |
| 20 | 1,3,5-Trichlorobenzene | 0.3 mol % | 10 min | 94.6% | Crystallization | tCP |

It has become apparent from these results that, according to the production process of the invention, organic photoconductors/organic electroluminescent element materials such as mCP, pCP, CBP, 26mCPy and tCP can be produced in a very short time (10 to 15 minutes) and in a high isolated yield (91.2 to 97.6%) by using an extremely small amount of the palladium catalyst (0.1 to 0.2 mol % per mol of a halogen atom in a (hetero)aryl halide).

Example 21

Production of N-Phenylindole (Structural Formula (25))

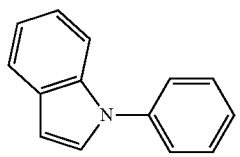

(25)

Non-Patent Literature 8 reported that, if a magnesium compound is used as a base when Indole which is one kind of NH-azoles and aryl halides are reacted in the presence of a palladium catalyst, C-arylindole (not N-arylindole) is obtained. Thus, the experimentation using indole as NH-azoles was performed.

[PdCl(π-allyl)]$_2$ (15.6 mg, 0.1 mol %) and cBRIDP (60.2 mg, 0.4 mol %) were placed into a 50 mL, two-necked, round bottomed flask equipped a gas inlet, and the flask was evacuated and filled with nitrogen. Subsequently, to the mixture was added dehydrated THF (11 mL) to prepare a catalyst solution. A 200 mL, four-necked, round-bottomed flask equipped with a Teflon® coated magnetic stirring bar, condenser, dropping funnel, thermometer, and a gas inlet was evacuated and filled with nitrogen. Indole (5.0 g, 42.7 mmol, 1.0 equivalent) and dehydrated toluene (55 mL) were charged into the flask, and the mixture was cooled to 5° C. using an ice bath. To the mixture was added a THF solution of tert-butylmagnesium chloride ($^t$BuMgCl) (1.02 mol/L, 46.0 mL, 47.0 mmol, 1.1 equivalents) (containing 42.0 mL of THF) dropwise via the dropping funnel at such a rate that the temperature of the reaction solution was kept at 15° C. or lower. Subsequently, to the solution were added chlorobenzene (4.8 mL, 47.0 mmol, 1.1 equivalents) and the catalyst solution (11 mL) successively, and the solution was stirred for 15 minutes under reflux. After cooling the reaction mixture to room temperature, to the mixture were added water (30 mL) and the aqueous layer was separated off. The organic layer was concentrated under reduced pressure to give oily residue, which was purified by silica gel column chromatography (eluent: n-hexane/toluene) to afford 7.9 g of phenylindole as a viscous oil.

Isolated yield: 96.0%.

$^1$H NMR (300 MHz, CDCl$_3$): 6.69 (dd, J=3.6, 0.9 Hz, 1H), 7.13-7.26 (m, 2H), 7.32-7.41 (m, 2H), 7.48-7.61 (m, 5H), 7.67-7.73 (m, 1H).

It has become apparent from the $^1$H NMR analysis result that, in spite of using a magnesium compound as a base, the product prepared by the production process of the invention is not C-phenylindole but is N-phenylindole.

Example 22

Production of 9-phenyl-2,3,4,9-tetrahydro-1H-carbazole (Structural Formula (26))

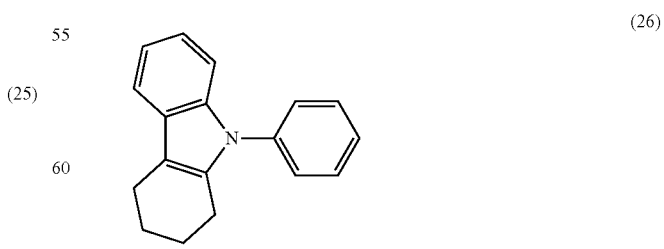

(26)

The reaction was conducted for 1 hours in the same experimental procedures as in Example 6 except for using 2,3,4,9-tetrahydro-1H-carbazole (11.1 g, 65.0 mmol, 1.03 equivalents) as the NH-azoles to afford 15.5 g of 9-phenyl-2,3,4,9-tetrahydro-1H-carbazole as a white solid.

Isolated yield: 99.3%.

$^1$H NMR (300 MHz, CDCl$_3$): 1.82-1.96 (m, 4H), 2.59-2.63 (m, 2H), 2.75-2.82 (m, 2H), 7.05-7.14 (m, 2H), 7.17-7.25 (m, 1H), 7.33-7.41 (m, 3H), 7.45-7.54 (m, 3H).

$^{13}$C NMR (75 MHz, CDCl$_3$): 21.1, 23.1, 23.2, 23.4, 109.8, 110.9, 117.7, 119.5, 121.2, 127.0, 127.2, 127.7, 129.3, 135.8, 137.2, 138.0.

Comparative Example 1

Comparative Experiment of Using Sodium Tert-Butoxide (NaO$^t$Bu) in Place of MeMgCl in the Production of N-Phenylcarbazole (Structural Formula (11)) (Reaction Formula 4)

Reaction Formula 4

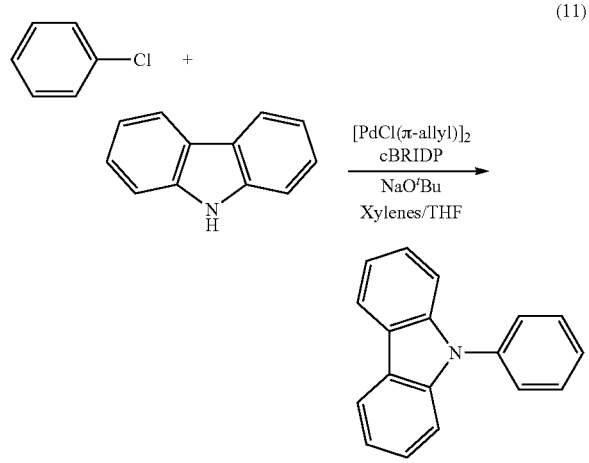

(11)

A comparative experiment was conducted by replacing MeMgCl used in Example 6 by NaO$^t$Bu. That is, [PdCl(π-allyl)]$_2$ (5.8 mg, 0.025 mol %) and cBRIDP (22.2 mg, 0.1 mol %) were placed into a 50 mL, two-necked, round bottomed flask equipped a gas inlet, and the flask was evacuated and filled with nitrogen. Subsequently, to the mixture was added dehydrated THF (8.2 mL, 101.0 mmol, 1.6 equivalents) to prepare a catalyst solution. A 200 mL, four-necked, round-bottomed flask equipped with a Teflon® coated magnetic stirring bar, condenser, dropping funnel, thermometer, and a gas inlet was evacuated and filled with nitrogen. Carbazole (10.9 g, 65.0 mmol, 1.03 equivalents), dehydrated xylenes (77 mL), dehydrated THF (17.3 mL, 213.6 mmol, 3.4 equivalents) [corresponding to the amount of THF contained in MeMgCl used in Example 6], NaO$^t$Bu (6.2 g, 64.4 mmol, 1.02 equivalents), chlorobenzene (6.4 mL, 63.1 mmol, 1.0 equivalent), and the catalyst solution (8.2 mL) were charged into the flask successively, and the mixture was stirred for 30 minutes under reflux. GC analysis to check progress of the reaction reveals that the conversion of the reaction was 0.9% in terms of chlorobenzene.

GC retention time: chlorobenzene: 2.4 minutes; N-phenylcarbazole: 17.1 minutes

Comparative Example 2

Comparative Experiment Using Potassium Carbonate (K$_2$CO$_3$) in Place of MeMgCl in the Production of N-Phenylcarbazole (Structural Formula (11)) (Reaction Formula 5)

Reaction Formula 5

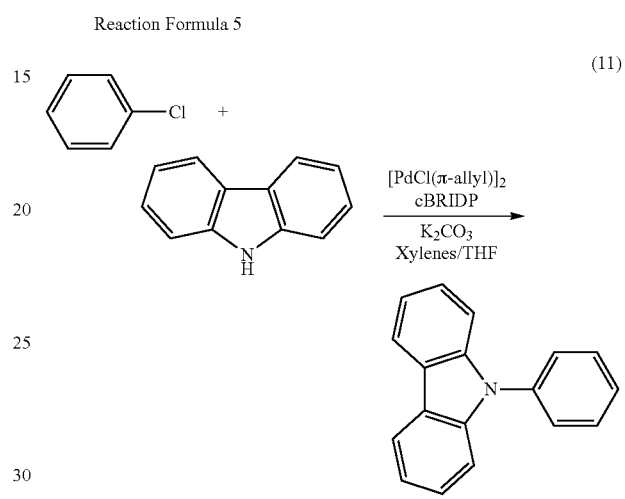

(11)

The reaction was conducted for 30 minutes in the same experimental procedures as in Comparative Example 1 except for using K$_2$CO$_3$ (8.9 g, 64.4 mmol, 1.02 equivalents) as a base. GC analysis to check progress of the reaction reveals that the conversion of the reaction was 2.2% in terms of chlorobenzene.

Comparative Example 3

Comparative Experiment Using NaO$^t$Bu in Place of $^t$BuMgCl in the Production of N-Phenylindole (Structural Formula (25)) (Reaction Formula 6)

Reaction Formula 6

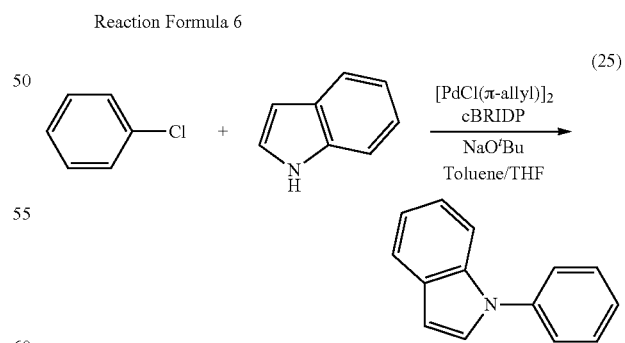

(25)

A comparative experiment was conducted by replacing $^t$BuMgCl used in Example 21 by NaO$^t$Bu. That is, {PdCl(π-allyl)}$_2$ (15.6 mg, 0.1 mol %) and cBRIDP (60.2 mg, 0.4 mol %) were placed into a 50 mL, two-necked, round bottomed flask equipped a gas inlet, and the flask was evacuated and filled with nitrogen. Subsequently, to the mixture was added dehydrated THF (11 mL) to prepare a catalyst solution. A 200 mL, four-necked, round-bottomed flask equipped with a Teflon® coated magnetic stirring bar, condenser, dropping funnel, thermometer, and a gas inlet was evacuated and filled with nitrogen. Indole (5.0 g, 42.7 mmol, 1.0 equivalent), dehydrated toluene (55 mL), dehydrated THF (42.0 mL) [corresponding to the amount of THF contained in $^t$BuMgCl used in Example 21], NaO$^t$Bu (4.5 g, 47 mmol, 1.1 equivalents), chlorobenzene (4.8 mL, 47.0 mmol, 1.1 equivalents), and the catalyst solution (11 mL) were charged into the flask successively, and the mixture was stirred for 15 minutes under reflux. GC analysis to check progress of the reaction reveals that the conversion of the reaction was 0.2% in terms of indole.

GC retention time: indole: 5.6 minutes; N-phenylindole: 11.7 minutes.

Comparative Example 4

Comparative Experiment Using K$_2$CO$_3$ in Place of $^t$BuMgCl in the Production of N-Phenylindole (Structural Formula (25)) (Reaction Formula 7)

Reaction Formula 7

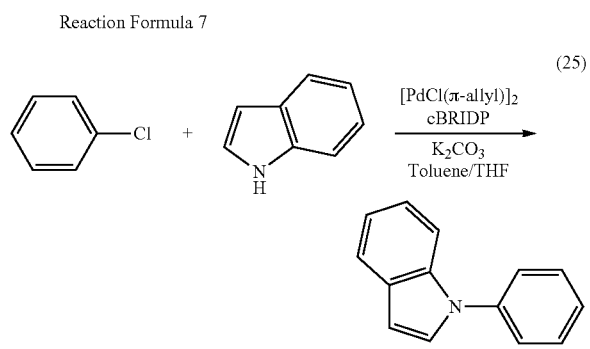

(25)

The reaction was conducted for 15 minutes in the same experimental procedures as in Comparative Example 3 except for using K$_2$CO$_3$ (6.5 g, 47.0 mmol, 1.1 equivalents) as a base. GC analysis to check progress of the reaction reveals that the conversion of the reaction was 2.5% in terms of indole.

The results of Examples 6 and 21 and Comparative Examples 1 to 4 are summarized in Table 4.

TABLE 4

| Comparative Example | Base | Reaction Conversion | Isolated Yield |
|---|---|---|---|
| 1 | NaO$^t$Bu | 0.9% | — |
| 2 | K$_2$CO$_3$ | 2.2% | — |
| (Example 6) | MeMgCl | >99.9% | 99.0% |
| 3 | NaO$^t$Bu | 0.2% | — |
| 4 | K$_2$CO$_3$ | 2.5% | — |
| (Example 21) | $^t$BuMgCl | >99.9% | 96.0% |

It has become apparent from these results that, when magnesium compounds such as MeMgCl and $^t$BuMgCl are used as a base upon production of an N-(hetero)arylazoles in the presence of a catalyst comprising a palladium compound and a coordination compound, the activity of the catalyst is improved markedly (40 to 500 times) in comparison with the case of using alkali metal compounds such as NaO$^t$Bu [which is being most popularly used in Buchwald-Hartwig amination (for example, Non-Patent Literatures 1, 2, 4, and 7)] and K$_2$CO$_3$ [which has been believed to be effective upon reacting aryl halides with NH-azoles in the presence of a palladium catalyst (Non-Patent Literature 5)] as a base.

While the invention has been described in detail and with reference to specific embodiments thereof, it will be apparent to one skilled in the art that various changes and modifications can be made therein without departing from the spirit and scope thereof.

This application is based on Japanese Patent Application No. 2011-191166 filed on Sep. 2, 2011, U.S. Provisional Application No. 61/531,737 filed on Sep. 7, 2011 and Japanese Patent Application No. 2012-185502 filed on Aug. 24, 2012, the entire subject matters of which are incorporated herein by reference. In addition, the subject matters of all documents cited in the specification are also incorporated here by reference.

INDUSTRIAL APPLICABILITY

According to the production process of the present invention, N-(hetero)arylazoles useful as medical or agrochemical products, organic photoconductor materials, organic electroluminescent element materials, or the like can be produced with low cost and high efficiency.

The invention claimed is:
1. A process for producing an N-arylazole or N-heteroarylazole, which comprises reacting a compound represented by the following general formula (5) with an azole in the presence of: a catalyst comprising a palladium compound and a monophosphine represented by the following general formula (1); a Grignard reagent represented by the following general formula (6'); and at least one solvent selected from the group consisting of a aliphatic hydrocarbon, an aromatic hydrocarbon and an ether, at a temperature range of 10° C. to 200° C.

(Het)Ar—X$_n$ (5)

wherein (Het)Ar represents an aromatic ring group or a heteroaromatic ring group, in which at least one hydrogen atom on the aromatic ring group or heteroaromatic ring group may be substituted by at least one group selected from the group consisting of an alkyl group, an alkenyl group, an alkynyl group, an aryl group, an aralkyl group, an aliphatic heterocyclic group, a heteroaryl group, an alkoxy group, an aryloxy group, an aralkyloxy group, a heteroaryloxy group, an acyl group, an alkylthio group, an arylthio group, an aralkylthio group, a heteroarylthio group, an amino group, a phosphino group, a silyl group, a boryl group, a cyano group and a fluoro group, X represents a group selected from the group consisting of a chloro group, a bromo group and a p-toluenesulfonyloxy group, a subscript n of X represents the number of the substituent X into (Het)Ar, and is an integer of from 1 to 3,

(1)

wherein P represents a phosphorus atom, R$^1$ and R$^2$ each independently represents a tertiary alkyl group, and R$^3$ represents a group selected from the group consisting of an alkyl group, alkenyl group, an aryl group, an aralkyl group, a pyrrolyl group, a pyrazolyl group, an indolyl group and a ferrocenyl group, in which at least one hydrogen atom on the aryl group, aralkyl group, pyrrolyl group, pyrazolyl group, indolyl group or ferrocenyl group may be substituted by a group selected from the group consisting of an alkyl group, an aryl group, an alkoxy group and an dialkylamino group, $$R^{12}\text{—Mg—X'} \qquad (6')$$

wherein Mg represents a magnesium atom; X' represents a group selected from the group consisting of a chloro group, a bromo group and an iodo group, and $R^{12}$ represents a group selected from the group consisting of an alkyl group, an alkenyl group, an aryl group and aralkyl group, in which at least one hydrogen atom on the alkenyl group, aryl group or aralkyl group may be substituted by an alkyl group, wherein the azole is selected from the group consisting of 1H-pyrrole, indole, carbazole, benzocarbazoles, dibenzocarbazoles, indolocarbazoles, biindoles and bicarbazoles, in which at least one hydrogen atom on a carbon atom of 1H-pyrrole, indole, carbazole, benzocarbazoles, dibenzocarbazoles, indolocarbazoles, biindoles or bicarbazoles may be substituted by at least one group selected from the group consisting of an alkyl group, an alkenyl group, an alkynyl group, an aryl group, an aralkyl group, an aliphatic heterocyclic group, a heteroaryl group, an alkoxy group, an aryloxy group, an aralkyloxy group, a heteroaryloxy group, an acyl group, an alkylthio group, an arylthio group, an aralkylthio group, a heteroarylthio group, an amino group, a phosphino group, a silyl group, a boryl group, a cyano group and a fluoro group wherein an amount of the palladium compound is 0.0001 equivalents or more and less than 0.01 equivalents in terms of palladium atom per the amount of the azole used.

2. The process according to claim 1, wherein the palladium compound is selected from the group consisting of bis(dibenzylideneacetone)palladium(0), tris(dibenzylideneacetone)dipalladium(0), tris(dibenzylideneacetone)dipalladium(0)-chloroform adduct, palladium(II) chloride, palladium(II) bromide, dichlorobis(acetonitrile)palladium(II), dichlorobis(benzonitrile)palladium(II), dichloro(1,5-cyclooctadiene)palladium(II), palladium(II) acetate, allylpalladium(II) chloride dimer, methallylpalladium(II) chloride dimer, crotylpallaldium(II) chloride dimer, and cinnamylpalladium(II) chloride dimer, and an amount of the palladium compound is 0.0001 equivalents or more and less than 0.01 equivalents in terms of palladium atom per the amount of the azole used.

3. The process according to claim 2, wherein the monophoshine represented by the general formula (1) is selected from the group consisting of tri-tert-butylphosphine, di-tert-butylmethylphosphine, di-tert-butylneopentylphosphine, 1-[2-(di-tert-butylphosphino)phenyl]-3,5-diphenyl-1H-pyrazole, 5-(di-tert-butylphosphino)-1',3',5'-triphenyl-1'H-[1,4']bipyrazole, [4-(N,N-dimethylamino)phenyl]di-tert-butylphosphine, (2-biphenyl)di-tert-butylphosphine, 2-di-tert-butylphosphino-2',4',6'-triisopropylbiphenyl, 2-di-tert-butylphosphino-2'-(N,N-dimethylamino)biphenyl, 2-(di-tert-butylphosphino)-3,6-dimethoxy-2',4',6'-triisopropyl-1,1'-biphenyl, 1,2,3,4,5-pentaphenyl-1'-(di-tert-butylphosphino)ferrocene, di(1-adamantyl)-n-butylphosphine, di(1-adamantyl)benzylphosphine, 2-(di-tert-butylphosphino)-1-phenylindole, 2-(di-tert-butylphosphino)-1-phenyl-1H-pyrrole, N-[2-di(1-adamantyl)phosphinophenyl]morpholine, di-tert-butyl(2,2-diphenyl-1-methylvinyl)phosphine, and di-tert-butyl(2,2-diphenyl-1-methyl-1-cyclopropyl)phosphine.

4. The process according to claim 3, wherein the Grignard reagent represented by the general formula (6') is selected from the group consisting of methylmagnesium chloride, methylmagnesium bromide, methylmagnesium iodide, ethylmagnesium chloride, ethylmagnesium bromide, n-propylmagnesium bromide, isopropylmagnesium chloride, isopropylmagnesium bromide, cyclopropylmagnesium bromide, n-butylmagnesium chloride, isobutylmagnesium bromide, sec-butylmagnesium bromide, tert-butylmagnesium chloride, n-pentylmagnesium bromide, cyclopentylmagnesium bromide, n-hexylmagnesium bromide, cyclohexylmagnesium bromide, n-heptylmagnesium bromide, n-octylmagnesium bromide, vinylmagnesium bromide, allylmagnesium chloride, allylmagnesium bromide, phenylmagnesium chloride, phenylmagnesium bromide, phenylmagnesium iodide, o-tolylmagnesium bromide, m-tolylmagnesium bromide, p-tolylmagnesium bromide, (2,5-dimethylphenyl)magnesium bromide, benzylmagnesium chloride, and benzylmagnesium bromide.

5. The process according to claim 4, wherein (Het)Ar in the compound represented by the general formula (5) represents a group selected from the group consisting of phenyl group, naphthyl group, anthryl group, phenanthrenyl group, pyrenyl group, perylenyl group, fluorenyl group, biphenyl group, binaphthyl group, bianthryl group, 9,9'-spirobi[9H-fluorene]-yl group, anthraquinolyl group, fluorenonyl group, furyl group, thienyl group, pyrrolyl group, pyridyl group, oxadiazolyl group, thiadiazolyl group, triazinyl group, benzofuryl group, dibenzofuryl group, benzothienyl group, dibenzothienyl group, indolyl group, carbazolyl group, quinolyl group, acridinyl group, phenanthridinyl group, benzoquinolinyl group, isoquinolinyl group, and benzoisoquinolinyl group.

6. The process according to claim 5, wherein a substituent that (Het)Ar in the compound represented by the general formula (5) may have and that the azole may have is selected from the group consisting of an alkyl group, an alkenyl group, an alkynyl group, an aryl group, an aralkyl group, an alkoxy group, an aryloxy group, an acyl group, an alkylthio group, an arylthio group, an amino group, a silyl group, a cyano group and a fluoro group.

* * * * *